(12) United States Patent
Benedict et al.

(10) Patent No.: US 9,415,139 B2
(45) Date of Patent: Aug. 16, 2016

(54) IMPLANTABLE MATERIALS FOR BONE REPAIR

(71) Applicant: Cerapedics, Inc., Westminster, CO (US)

(72) Inventors: James J. Benedict, Detroit Lakes, MN (US); Nolan Chase Hannigan, Lakewood, CO (US); Katherine Suzanne Davis, Boudler, CO (US); Whitney Terese Young, Arlington, MA (US)

(73) Assignee: Cerapedics, Inc., Westminster, CO (US)

( * ) Notice: Subject to any disclaimer, the term of this patent is extended or adjusted under 35 U.S.C. 154(b) by 0 days.

(21) Appl. No.: 13/724,704

(22) Filed: Dec. 21, 2012

(65) Prior Publication Data

US 2013/0244942 A1    Sep. 19, 2013

Related U.S. Application Data

(60) Provisional application No. 61/579,806, filed on Dec. 23, 2011.

(51) Int. Cl.
| | |
|---|---|
| *A61L 27/58* | (2006.01) |
| *A61L 27/42* | (2006.01) |
| *A61K 38/39* | (2006.01) |
| *A61L 27/12* | (2006.01) |
| *A61L 27/36* | (2006.01) |
| *A61L 27/46* | (2006.01) |
| *A61L 27/52* | (2006.01) |

(52) U.S. Cl.
CPC .............. *A61L 27/58* (2013.01); *A61K 38/39* (2013.01); *A61L 27/12* (2013.01); *A61L 27/3608* (2013.01); *A61L 27/427* (2013.01); *A61L 27/46* (2013.01); *A61L 27/52* (2013.01); *A61L 2430/02* (2013.01)

(58) Field of Classification Search
CPC ................ A61F 2002/2835; A61F 2002/2839; A61L 24/02
See application file for complete search history.

(56) References Cited

U.S. PATENT DOCUMENTS

| | | |
|---|---|---|
| 7,628,851 B2 | 12/2009 | Armitage et al. |
| 2004/0259972 A1 | 12/2004 | Ringeisen et al. |
| 2007/0041906 A1 | 2/2007 | Lidgren et al. |
| 2007/0098799 A1 | 5/2007 | Zhang et al. |
| 2007/0141103 A1 | 6/2007 | Benedict et al. |
| 2009/0175944 A1 | 7/2009 | Ringeisen et al. |
| 2011/0027332 A1 | 2/2011 | Benedict et al. |
| 2011/0046686 A1 | 2/2011 | Kaplan et al. |

FOREIGN PATENT DOCUMENTS

WO    WO 2009/100280    *    8/2009    .............. A61L 27/14

OTHER PUBLICATIONS

International Search Report and Written Opinion for International Application No. PCT/US2012/071300, dated Apr. 5, 2013 (16 pages).

(Continued)

*Primary Examiner* — Allison Fox
(74) *Attorney, Agent, or Firm* — Kristina Bieker-Brady; Clark & Elbing LLP

(57) ABSTRACT

The invention features fiber reinforced bone repair putties and fiber reinforced pliable lyophilized implants which are useful for the treatment of bone defects. The putties and lyophilized implants include ceramic particles. The formulations of the invention can exhibit reduced migration of the ceramic particles, and are mechanically strengthened so the materials can be aggressively manipulated by a physician during an implantation procedure without tearing or puncturing.

38 Claims, 7 Drawing Sheets

(56) References Cited

OTHER PUBLICATIONS

Examination Report for Australian Application No. 2012358294, mailed Dec. 11, 2015 (3 pages).

Extended European Search Report for European Patent Application No. 12860704.1, dated Jan. 14, 2016 (8 pages).

International Preliminary Report on Patentability for International Patent Application No. PCT/US2012/071300, issued Dec. 2, 2014 (7 pages).

* cited by examiner

SEQUENCE LISTING

<160> NUMBER OF SEQ ID NOS: 24

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Gly Thr Pro Gly Pro Gln Gly Ile Ala Gly Gln Arg Gly Val Val
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Gly Pro Gln Gly Ile Ala Gly Gln Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Gln Gly Ile Ala Gly Gln
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Gln Gly Ile Ala Gly Gln Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Phe Gly Ile Ala Gly Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Gly Ile Ala Gly Gln
1               5

```
<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Gln Gly Ala Ile Ala Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Phe Gly Ile Ala Gly Phe
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Cys Gly Ile Ala Gly Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Glu Gly Ile Ala Gly Lys
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: ACETYLATION
<222> LOCATION: (1)..(1)
<223> OTHER INFORMATION: N-acetyl Isoleucine

<400> SEQUENCE: 11

Ile Ala Ala
1

<210> SEQ ID NO 12
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (3)..(3)
<223> OTHER INFORMATION: beta.Ala

<400> SEQUENCE: 12

Ile Ala Ala
1

<210> SEQ ID NO 13
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: ACETYLATION
<222> LOCATION: (1)..(1)
<223> OTHER INFORMATION: N-acetyl Isoleucine
<220> FEATURE:
<221> NAME/KEY: METHYLATION
<222> LOCATION: (2)..(2)
<223> OTHER INFORMATION: alanyl-methylamide

<400> SEQUENCE: 13

Ile Ala
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct

<400> SEQUENCE: 14

Asp Gly Glu Ala
1

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Asp Gly Glu Ala Gly Cys
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Pro is hydroxyproline

<400> SEQUENCE: 16

Gly Phe Pro Gly Glu Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (3)..(3)
<223> OTHER INFORMATION: Pro is hydroxyproline

<400> SEQUENCE: 17

Gly Leu Pro Gly Glu Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Pro is hydroxyproline

<400> SEQUENCE: 18

Gly Met Pro Gly Glu Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Ala or Leu

<400> SEQUENCE: 19

Gly Xaa Ser Gly Glu Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Pro is hydroxyproline

<400> SEQUENCE: 20

Gly Ala Pro Gly Glu Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21

Tyr Ile Gly Ser Arg
1               5

<210> SEQ ID NO 22
<211> LENGTH: 5
<212> TYPE: PRT
<213> ORGANISM: Artificial Sequence
```

```
<220> FEATURE:
<223> OTHER INFORMATION: Synthetic Construct

<400> SEQUENCE: 22

Gly Arg Gly Asp Ser
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Trp Gln Pro Pro Arg Ala Arg Ile
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic Construct

<400> SEQUENCE: 24

Arg Glu Asp Val
1
```

IMPLANTABLE MATERIALS FOR BONE REPAIR

CROSS REFERENCE TO RELATED APPLICATIONS

This application claims benefit from U.S. provisional application Ser. No. 61/579,806, filed Dec. 23, 2011, and incorporated herein by reference.

BACKGROUND OF THE INVENTION

The invention relates to the field of bone void fillers, and their use for the treatment of orthopedic conditions.

Physicians are sometimes called upon to repair bone that has been damaged by disease, trauma, osseous surgery or other causes, or to cause bone material to grow where there has been no bone before, such as during a spine fusion procedure. As an outcome of that procedure, it is desirable for two or more vertebral bodies to be maintained in a specific orientation. This can be accomplished by growing a column or bridge of rigid bone between the vertebral bodies. This maintains them in a fixed position relative to each other. The repair of long bone fractures can often be accomplished merely by relocating disrupted bone elements into natural proximity and fixing them in place until they can heal together. This is the approach taken in repairing ordinary limb fractures, for example. The fractured bone is re-set, then immobilized for a period of weeks in a rigid or semi-rigid cast or splint as the fractured elements heal.

Sometimes, however, this approach is insufficient because the patient has lost some of the bone. This can happen in certain kinds of trauma where the bone is so badly shattered that it cannot feasibly be pieced together. More often, it happens as a result of disease that destroys bone mass or as the result of osseous surgery in which destruction of bone mass is unavoidable. In these cases, there is no patient bone to re-set into proper position for healing. Instead, there is a void or defect that must somehow be filled, or a gap between two bone structures that needs to be filled with new bone. The filling of this defect or gap requires a material that is not only biocompatible but preferably will accept or even promote in-growing natural bone as the site heals. In such a mariner, the material ideally will eventually become resorbed as new in-growing natural bone takes its place as part of the skeletal structure. Completely resorbed material eliminates the possibility for a stress riser that can occur when foreign matter remains in the skeleton, potentially giving rise to a fracture in the future.

Numerous bone replacement materials have been employed by physicians with varying degrees of success. One approach is to use bone material recovered from the patient himself, or so-called autologous bone. This approach is advantageous in that it avoids biocompatibility and bio-rejection problems. However, such an approach necessarily involves two surgical procedures, two surgical sites, and two healing processes—one for the original injury and a second for the site of the donated bone material. This means greater cost, and increased risk of infection and morbidity for a patient that is already seriously ill or injured. Also, this approach can require a great deal of time and surgical skill as the surgeon removes the donated material from the donation site, shapes and fits it to the primary site, and then repairs both sites. Finally, there is quite obviously a limit to the amount of bone in the patient's body available to be sacrificed as donor material.

Alternatively, a particulate bone graft substitute can be used to fill the bone defect. The selection of the particulate bone graft substitute depends upon its intended function in the treatment, its biocompatibility with the human body and its availability. A key limitation is whether the function of the treatment requires that the material be resorbed by natural bodily actions or remain in place as permanent supporting structures. Of the useful ceramic particulates, allogenic material is readily available and, alternatively, xenogeneic bone sources are utilized as well. Synthetic materials, principally hydroxyapatite are also available. The ceramic particulates, unformulated, are available as dry granules and generally lack sufficient cohesiveness and adhesion for filling an osseous defect. Therefore, they are often mixed with an appropriate carrier.

In general, formulators of bone treatment materials have directed a great deal of effort to improve handling characteristics through selection of an appropriate carrier for delivering the bone repair material to the defect site. It is desirable that the bone repair material be easily placed, but not be allowed to migrate from the defect. In addition, and primarily, bone formation must not be inhibited by the carrier. That is, the carrier materials for the bone repair material must be biocompatible and not interfere with the mediated bone formation, while helping provide adequate spacing between the repair material particulates to allow for cell and vascular infiltration. The carrier material should biodegrade and be resorbed. However, too fast a degradation rate is not preferred since cellular and vascular infiltration cannot develop. Too slow of a resorption rate also interferes with cellular migration, vascular penetration and bone formation.

There remains a need for bone repair treatment formulations that include high concentrations of resorbable ceramic particulates in a carrier that, when applied to a defect site, remains with minimal migration of the ceramic particulates from the site of implantation.

SUMMARY OF THE INVENTION

The invention features fiber reinforced bone repair putties and fiber reinforced pliable lyophilized implants which are useful for the treatment of bone defects. The putties and lyophilized implants include ceramic particles. The formulations of the invention can exhibit reduced migration of the ceramic particles, and are mechanically strengthened so the materials can be aggressively manipulated by a physician during an implantation procedure without tearing or puncturing.

In a first aspect, the invention features a bone repair putty including: (i) from 25% to 65% (w/w) (e.g., 25% to 35%, 35% to 45%, 45% to 55%, or 55% to 65% (w/w)) particulate bone graft substitute or particulate demineralized bone matrix having a mean particle size of from 100 μm to 1000 μm (e.g., 150±50, 250±50, 350 ±50, 450±50, 550±50 μm, 600±50 μm, or 750±250 μm); (ii) from 30% to 75% (w/w) (e.g., 30% to 40%, 40% to 50%, 50% to 60%, 60% to 70%, or 65% to 75% (w/w)) hydrogel carrier for suspending the particulate bone graft substitute; and (iii) from 0.2% to 2% (w/w) (e.g., 0.2% to 0.6%, 0.5% to 0.9%, 0.8% to 1.2%, or 1.1% to 2.0% (w/w)) fibers, the fibers having an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm), wherein the bone repair putty is non-setting and malleable and wherein the migration of the ceramic particles from the putty is reduced. The fiber reinforced putties of the invention can exhibit reduced migration or no migration in vivo, and can exhibit a reduced migration time in vitro. In particular embodiments, the hydrogel carrier includes a dispersing agent selected from glycerin, polyethylene glycol, N-methyl pyrrolidone, and triacetin; a polymer selected from sodium carboxymethylcellulose, polyvinylalcohol, hydroxyethyl cellulose, hydroxypropyl methylcellulose, methylcellulose, ethylcellulose, and hyaluronic acid; and water. For example, the bone repair putty can include: (i) from 3% to 10% (w/w) (e.g., 3% to 5%, 4.5% to 7%, 6% to 8%, or 7% to 10% (w/w)) a dispersing agent selected from glycerin, polyethylene glycol, N-methylpyrrolidone, and triacetin; (ii) from 0.5% to 8.0% (w/w) (e.g., 0.5% to 1.5%, 1.0% to 3.0%, 2.0% to 5.0%, or 4.0% to 8.0% (w/w)) a polymer selected from sodium carboxymethylcellulose, polyvinylalcohol, hydroxyethyl cellulose, hydroxypropyl methylcellulose, methylcellulose, ethylcellulose, and hyaluronic acid; (iii) from 40% to 60% (w/w) (e.g., 40% to 45%, 40% to 50%, 45% to 55%, 50% to 60%, or 55% to 60% (w/w)) particulate calcium phosphate; (iv) from 25% to 55% (w/w) (e.g., 25% to 35%, 30% to 40%, 35% to 45%, 40% to 55%, or 45% to 55% (w/w)) water; and (v) from 0.2% to 2% (w/w) (e.g., 0.2% to 0.6%, 0.5% to 0.9%, 0.8% to 1.2%, or 1.1% to 2.0% (w/w)) fibers, the fibers having an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm). The particulate bone graft substitute can be any synthetic or natural calcium-containing mineral. The particulate bone graft substitute can be selected from hydroxyapatite particles, dahllite particles, tetracalcium phosphate particles, calcium pyrophosphate particles, tricalcium phosphate particles, calcium hydrogen phosphate particles, octacalcium phosphate particles, calcium fluorapatite particles, and mixtures thereof. For example, the particulate bone graft substitute can be hydroxyapatite particles having diameters between 250 microns to 425 microns, such as anorganic bone mineral coated with P-15 peptide. In particular embodiments, the bone repair putty includes the polymer sodium carboxymethylcellulose and the dispersing agent glycerin. The bone repair putty can include: (i) from 4.5% to 7.5% (w/w) glycerin; (ii) from 1.0% to 2.0% (w/w) sodium carboxymethylcellulose; (iii) from 45% to 65% (w/w) anorganic bone mineral; and (iv) from 0.2% to 2% (w/w) (e.g., 0.2% to 0.6%, 0.5% to 0.9%, 0.8% to 1.2%, or 1.1% to 2.0% (w/w)) fibers, the fibers having an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm); and (v) from 35% to 45% (w/w) water. The fibers can be, without limitation, selected from silk fibers (e.g., textile silk or surgical silk), cellulose fibers, nylon fibers, collagen fibers, elastin fibers, gelatin fibers, keratin fibers, hyaluronan fibers, alginate fibers, glyco-lactide fibers, chitosan fibers, polyethylene fibers, polyurethane fibers, polyglycolide fibers, poly-l-lactide fibers, poly-β-hydroxybutyric acid fibers, polydioxanone fibers, polyester fibers (e.g., PLLA, PGA, PLG, PCL, PMA, PET, and PLA), polycarbonate fibers, dacron fibers, bio-active glass fibers, gold fibers, carbon fibers, nitinol fibers, and stainless steel fibers. For example, the putty can include from 0.75% to 1.25% (w/w) (e.g., 0.75% to 0.90%, 0.85% to 0.95%, 0.90% to 1.05%, or 1.0% to 1.25% (w/w)) silk fibers having an average length of from 7 to 12 mm (e.g., 7±2, 8±2, 9±2, 10±2, 11±2, or 12±2 mm). In particular embodiments, the fibers have an average diameter of from 5 μm to 60 μm (e.g., from 5 μm to 20 μm, 15 μm to 30 μm, 20 μm to 40 μm, or 35 μm to 60 μm). In certain embodiments of the bone repair putties of the invention, the particulate includes particles and the ratio of the number particles to the number of fibers in the putty is from 0.1 to 10 (e.g., 0.25 to 4, 0.5 to 2, 0.75 to 1.25, or from 0.9 to 1.1).

In a related aspect, the invention features a pliable implantable composition for correcting bone defects formed by lyophilizing the bone repair putty of the invention. In particular embodiments, the pliable implantable composition has a load at failure (LAF) ratio of $LAF_{dry}$ to $LAF_{wet}$ of from 1.5 to 15 (e.g., 1.5 to 3, 2.5 to 6, 5 to 9, or 8 to 15). In still other embodiments, the ratio of $LAF_{FR}$ to $LAF_{fiberless}$ is from 3 to 100 (e.g., 3 to 12, 10-15, 15 to 22, or 22 to 35, or 35 to 100). In still other embodiments, the pliable implantable composition has a yield stress (YS) ratio of $YS_{FR}$ to $YS_{fiberless}$ of from 3 to 15 (e.g., 5±2, 7±2, 9±2, 11±2, 13±2, or 15±2). The pliable implantable composition can have a modulus (M) ratio of $M_{FR}$ to $M_{fiberless}$ of from 5 to 40 (e.g., 8±3, 15±5, 20±5, 25±5, 30±5, 35±5, or 40±5). The fiber reinforced pliable implantable compositions of the invention can exhibit reduced migration or no migration in vivo, and can exhibit a reduced migration time in vitro.

The invention further features a pliable implantable composition for correcting bone defects including: (i) from 5% to 20% (w/w) (e.g., 5% to 10%, 10% to 15%, or 15% to 20% (w/w)) a dispersing agent selected from glycerin, polyethylene glycol, N-methylpyrrolidone, and triacetin; (ii) from 1.0% to 6.0% (w/w) (e.g., 1.0% to 1.5%, 1.5% to 2.5%, 2.5% to 4.5%, or 3.5% to 6.0% (w/w)) a polymer selected from sodium carboxymethylcellulose, polyvinylalcohol, hydroxyethyl cellulose, hydroxypropyl methylcellulose, methylcellulose, ethylcellulose, and hyaluronic acid; (iii) from 65% to 90% (w/w) (e.g., 65% to 75%, 75% to 85%, 80% to 90%, or 85% to 90% (w/w)) particulate bone graft substitute or particulate demineralized bone matrix having a mean particle size of from 100 μm to 1000 μm (e.g., 150±50, 250±50, 350±50, 450±50, 550±50 μm, 600±50 μm, or 750±250 μm); and (iv) from 0.2% to 3.5% (w/w) (e.g., 0.2% to 0.6%, 0.5% to 0.9%, 0.8% to 1.2%, 1.1% to 2.0%, 1.5% to 2.2%, 1.9% to 2.7%, or 2.4% to 3.5% (w/w)) fibers, the fibers having an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm), wherein the pliable implantable composition has a porosity of from 5 to 35% and includes from 1.5% to 20% (w/w) (e.g., from 1.5% to 6%, 5% to 9%, 8% to 12%, or 11% to 20% (w/w)) water. In particular embodiments, the mean pore size in the pliable implantable composition is from about 25 μm to about 200 μm. The particulate bone graft substitute can be selected from hydroxyapatite particles, dahllite particles, tetracalcium phosphate particles, calcium pyrophosphate particles, tricalcium phosphate particles, calcium hydrogen phosphate particles, octacalcium phosphate particles, calcium fluorapatite particles, and mixtures thereof. For example, the particulate bone graft substitute can be hydroxyapatite particles having diameters between 250 microns to 425 microns. In one particular embodiment, the particulate bone graft substitute is anorganic bone mineral coated with P-15 peptide. In certain embodiments, the polymer is sodium carboxymethylcellulose and the dispersing agent is glycerin. For example, the composition can include: (i) from 8% to 15% (w/w) (e.g., 8.0% to 9.5%, 9.5% to 12.5%, or 12.5% to 15% (w/w)) glycerin; (ii) from 1.5% to 3.0% (w/w) (e.g., 1.5% to 1.75%, 1.75% to 2.25%, 2.25% to 2.75%, or 2.75% to 3.0% (w/w)) sodium carboxymethylcellulose; (iii) from 75% to 90% (w/w) (e.g., 75% to 80%, 80% to 85%, or 85% to 90% (w/w)) anorganic bone mineral; and (iv) from 0.2% to 3.5% (w/w) (e.g., 0.2% to 0.6%, 0.5% to 0.9%, 0.8% to 1.2%, 1.1% to 2.0%, 1.5% to 2.2%, 1.9% to 2.7%, or 2.4% to 3.5% (w/w)) fibers, the fibers having an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm); and (v) from 1.5% to 6% (w/w) (e.g., 1.5% to 2.5%, 2.25% to 3.25%, 3.25% to 4.75%, or 4.75% to 6.0% (w/w)) water. The fibers can be, without limitation, selected from silk fibers (e.g., textile silk or surgical silk), cellulose fibers, nylon fibers, and polyester fibers (e.g., PLLA or PGA). For example, the pliable implantable composition can include from 1.2% to 1.8% (w/w) (e.g., 1.2% to 1.5% or 1.4% to 1.7%, (w/w)) silk fibers having an average length of from 7 to 12 mm (e.g., 7±2, 8±2, 9±2, 10±2, 11±2, or 12±2 mm). In particular embodiments, the fibers have an average diameter of from 5 µm to 60 µm (e.g., from 5 µm to 20 µm, 15 µm to 30 µm, 20 µm to 40 µm, or 35 µm to 60 µm). In certain embodiments of the pliable implantable compositions of the invention, the particulate includes particles and the ratio of the number particles to the number of fibers in the putty is from 0.1 to 10 (e.g., from 0.25 to 4, 0.5 to 2, 0.75 to 1.25, or from 0.9 to 1.1). In particular embodiments, the pliable implantable composition has a ratio of $LAF_{dry}$ to $LAF_{wet}$ of from 1.5 to 15 (e.g., 1.5 to 3, 2.5 to 6, 5 to 9, or 8 to 15). In still other embodiments, the ratio of $LAF_{FR}$ to $LAF_{fiberless}$ is from 3 to 100 (e.g., 3 to 12, 10-15, 15 to 22, or 22 to 35, or 35 to 100). In still other embodiments, the pliable implantable composition has a yield stress (YS) ratio of $YS_{FR}$ to $YS_{fiberless}$ of from 3 to 15 (e.g., 7±2, 9±2, 11±2, 13±2, or 15±2). The pliable implantable composition can have a modulus (M) ratio of $M_{FR}$ to $M_{fiberless}$ of from 5 to 40 (e.g., 20±5, 25±5, 30±5, 35±5, or 40±5). The fiber reinforced pliable implantable compositions of the invention can exhibit reduced migration or no migration in vivo, and can exhibit a reduced migration time in vitro.

In certain embodiments of any of the above compositions, the composition includes both a particulate bone graft substitute that is a synthetic or naturally occurring calcium-containing mineral and particulate demineralized bone matrix.

In one particular embodiment of any of the above compositions, the particulate bone graft substitute is coated with a cell adhesion peptide derived from a binding domain of a cell adhesion protein of an extracellular matrix (e.g., fibronectin, vitronectin, laminin, elastin, fibrinogen, collagen type I, collagen type II, or collagen type V). For example, the cell adhesion peptide can include an amino acid sequence selected from arginine-glycine-aspartate (RGD) and tyrosine-isoleucine-glycine-serine-arginine (YIGSR)(SEQ ID NO: 21). In particular embodiments, the cell adhesion peptide is an α2β1 or α1β1 binding collagen mimetic peptide. Exemplary collagen mimetic peptides include, without limitation, peptides including an amino acid sequence selected from DGEA (SEQ ID NO: 14), GFOGER (SEQ ID NO: 16), GLOGER (SEQ ID NO: 17), GMOGER (SEQ ID NO: 18), GLSGER (SEQ ID NO. 19), GASGER (SEQ ID NO: 19), GAOGER (SEQ ID NO: 20), and GTPGPQ-GIAGQRGVV (P15) (SEQ ID NO. 1), or a bioactive fragment thereof. Alternatively, a cell adhesion peptide may be covalently or non-covalently attached (i.e., complexed) to the fiber in the formulation of the invention.

In another particular embodiment of any of the above compositions, the fibers include a cell adhesion peptide derived from a binding domain of a cell adhesion protein of an extracellular matrix (e.g., fibronectin, vitronectin, laminin, elastin, fibrinogen, collagen type I, collagen type II, or collagen type V). For example, the cell adhesion peptide can include an amino acid sequence selected from arginine-glycine-aspartate (RGD) and tyrosine-isoleucine-glycine-serine-arginine (YIGSR) (SEQ ID NO: 21). In particular embodiments, the cell adhesion peptide is an α2β1 or α1β1 binding collagen mimetic peptide. Exemplary αcollagen mimetic peptides include, without limitation, peptides including an amino acid sequence selected from DGEA (SEQ ID NO: 14), GFOGER (SEQ ID NO: 16), GLOGER (SEQ ID NO: 17), GMOGER (SEQ ID NO: 18), GLSGER (SEQ ID NO: 19), GASGER (SEQ ID NO: 19), GAOGER (SEQ ID NO: 20), and GTPG-PQGIAGQRGVV (P15) (SEQ ID NO: 1), or a bioactive fragment thereof. The cell adhesion peptide may be covalently or non-covalently attached (i.e., complexed) to the fiber in the formulation of the invention.

In certain embodiments of any of the above compositions, the compositions include silk fibers including P-15 peptide. The composition may further include a particulate bone graft substitute, such as anorganic bone mineral, coated with P-15 peptide.

In particular embodiments of any of the above bone repair putties, the bone repair putty is extrusion processed.

In particular embodiments of any of the above pliable implantable compositions, the pliable implantable composition formed from an extrusion processed bone repair putty.

The invention further features a method for correcting a bone defect in a subject by implanting into the subject an implantable composition of the invention at the site of the bone defect. The bone defect can be any type of bone defect described herein.

By "collagen mimetic peptide" is meant a synthetic peptide of from 3 to 50 amino acid residues having affinity for α2β1 integrin. α2β1 collagen mimetic peptides include, without limitation, peptides including the peptide sequences of any of SEQ ID NOS. 1-20: Gly-Thr-Pro-Gly-Pro-Gln-Gly-Ile-Ala-Gly-Gln-Arg-Gly-Val-Val (SEQ ID NO. 1, also known as "P-15"), Gly-Pro-Gln-Gly-Ile-Ala-Gly-Gln-Arg (SEQ ID NO: 2), Gln-Gly-Ile-Ala-Gly-Gln (SEQ ID NO: 3), Gln-Gly-Ile-Ala-Gly-Gln-Arg (SEQ ID NO: 4), Phe-Gly-Ile-Ala-Gly-Phe (SEQ ID NO: 5), Gly-Ile-Ala-Gly-Gln (SEQ ID NO: 6), Gln-Gly-Ala-Ile-Ala-Gln (SEQ ID NO: 7), Phe-Gly-Ile-Ala-Gly-Phe (SEQ ID NO:8), Cys-Gly-Ile-Ala-Gly-Cys (SEQ ID NO:9), Glu-Gly-Ile-Ala-Gly-Lys (SEQ ID NO:10), N-Acetyl Ile-Ala-Ala (SEQ ID NO:11), Ile-Ala-.beta.Ala (SEQ ID NO:12), N-Acetyl Ile-Ala NMe (SEQ ID NO:13), Asp-Gly-Glu-Ala (SEQ ID NO:14), Asp-Gly-Glu-Ala-Gly-Cys (SEQ ID NO:15), Gly-Phe-Pro*-Gly-Glu-Arg (SEQ ID NO:16, where Pro*=hydroxyproline), Gly-Leu-Pro*-Gly-Glu-Arg (SEQ ID NO:17, where Pro*=hydroxyproline), Gly-Met-Pro*-Gly-Glu-Arg (SEQ ID NO:18, where Pro*=hydroxyproline), Gly-Ala-Ser-Gly-Glu-Arg (SEQ ID NO:19), Gly-Leu-Ser-Gly-Glu-Arg (SEQ ID NO:19), Gly-Ala-Pro*-Gly-Glu-Arg (SEQ ID NO:20, where Pro*=hydroxyproline), and any other α2β1 collagen mimetic peptides described in U.S. Pat. No. 7,199,103, incorporated herein by reference.

As used herein, the term "cell adhesion peptide" refers to peptides of 3 to 100 amino acid residues in length (e.g., from 3 to 80, from 3 to 60, from 3 to 50, or from 3 to 40 amino acid residues in length) which are capable of binding to anchorage dependent cells via cell surface molecules, such as integrins, displayed on the surface of anchorage dependent cells.

As used herein, the term "extrusion processed" refers to the method of passing a fiber reinforced bone repair putty of the invention through an orifice sized to form lengths (e.g., strings or ropes or ribbons of extruded material using an orifice of about 2±1 mm, 4±1 mm, 6±2 mm, 10±2 mm, or 12±3 mm in its largest dimension) or sheets (e.g., using an orifice that is 4±2 mm×25±8 mm). The lengths may be laid side-by-side and pressed into any desired predetermined shape prior to implantation. Optionally, the lengths are lyophilized to form a pliable implantable composition.

As used herein, the term "particulate demineralized bone matrix" refers to bone particles that have had some portion of their original mineral content removed by a demineralization process. Demineralization removes the inorganic mineral component of bone by employing acid solutions (see Reddi et al., Proc. Nat. Acad. Sci. 69:1601 (1972)). The strength of the acid solution, the shape of the bone particles and the duration of the demineralization treatment can determine the extent of demineralization (see Lewandrowski et al., J Biomed Materials Res. 31:365 (1996)).

As used herein, the term "ratio of $LAF_{FR}$ to $LAF_{fiberless}$" refers to the ratio of the load at failure for a fiber reinforced formulation of the invention ($LAF_{FR}$) to the load at failure for a fiberless lyophilized formulation containing 81-84% (w/w) ABM/P-15; 2.3-2.5% (w/w) sodium carboxymethylcellulose; 11.0-11.3% (w/w) glycerol; and 3-5% water.

As used herein, the term "ratio of $YS_{FR}$ to $YS_{fiberless}$" refers to the ratio of the yield stress for a fiber reinforced formulation of the invention ($YS_{FR}$) to the yield stress for a fiberless lyophilized formulation containing 81-84% (w/w) ABM/P-15; 2.3-2.5% (w/w) sodium carboxymethylcellulose; 11.0-11.3% (w/w) glycerol; and 3-5% water.

As used herein, the term "ratio of $M_{FR}$ to $M_{fiberless}$" refers to the ratio of the modulus for a fiber reinforced formulation of the invention ($YS_{FR}$) to the modulus for a fiberless lyophilized formulation containing 81-84% (w/w) ABM/P-15; 2.3-2.5% (w/w) sodium carboxymethylcellulose; 11.0-11.3% (w/w) glycerol; and 3-5% water.

As used herein, the term "ratio of $LAF_{dry}$ to $LAF_{wet}$" refers to the ratio of the load at failure for a dry fiber reinforced formulation of the invention ($LAF_{dry}$) to the load at failure for the same formulation when wet using the method described in Example 2.

As used herein, the term "reduced migration" refers to a reduction in the observed in vivo migration of ceramic particles for a fiber reinforced formulation of the invention in comparison to the performance of the same formulation, except with the fibers removed, in the PLIF procedure described in Example 10. By "no migration" is meant no observed in vivo migration of ceramic particles in the PLIF test of Example 10.

As used herein, the term "reduced extrusion time" refers to refers to a reduction in the in vitro extrusion rate of a fiber reinforced putty of the invention in comparison to the performance of the same formulation, except with the fibers removed, in the in vitro method described in Example 6. For example, the extrusion time for a fiber reinforced putty of the invention can be 3±0.5 minutes, 4±0.5 minutes, 5±0.5 minutes, 6±0.5 minutes, 7±0.5 minutes, or 8±0.5 minutes.

Other features and advantages of the invention will be apparent from the following detailed description, the drawings, and the claims.

DRAWINGS

Figure 4A:
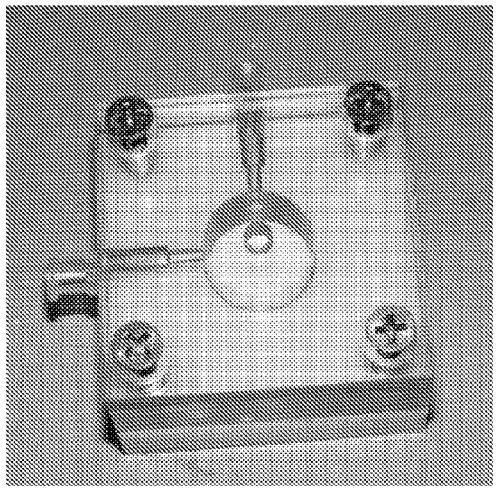
Figure 4B:
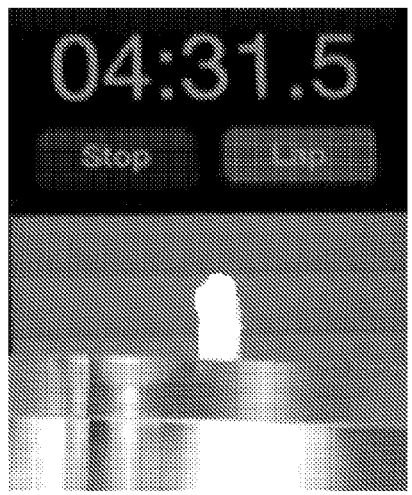
Figure 4C:
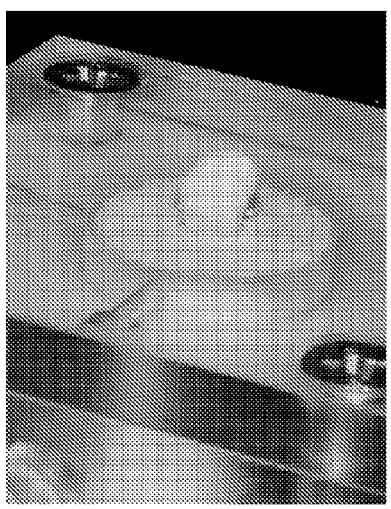
Figure 4D:
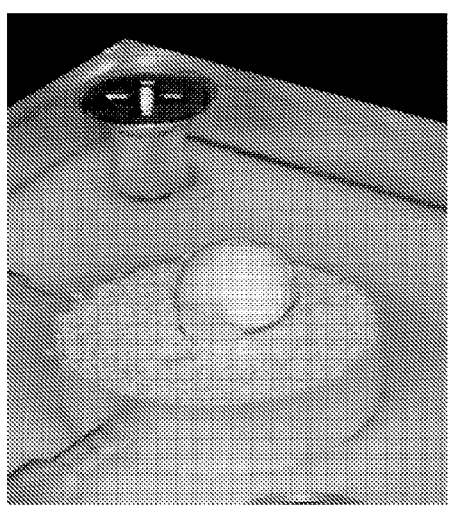

FIGS. 4A-4D are pictures of an in-vitro particle extrusion testing device described in Example 6. FIG. 4B is a picture depicting the performance of fiberless putty. FIG. 4C is a picture depicting the performance of 0.5 wt % silk fiber reinforced (SFR) Putty. FIG. 4D is a picture depicting the performance of 1.0 wt % SFR Putty. These photographs were taken after extrusion occurred, at different time points for each photograph.

Figure 5:
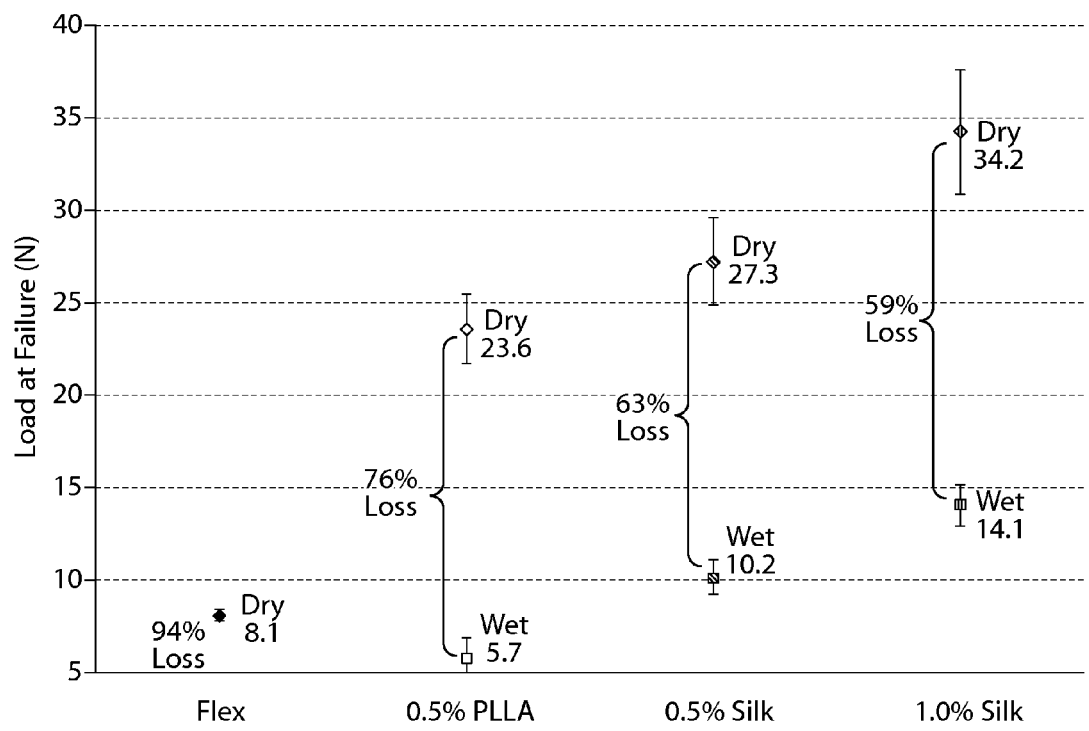

FIG. 5 is a drawing depicting the load at failure (LAF) of samples in the BPD test (see Example 9). The testing of the fiberless Flex formulation was not performed wet, the LAF being consistently very low (i.e., 0.5 N). Upper and lower error bars are for dry and wet samples, respectively, and represent 95% confidence intervals.

Figure 6A:
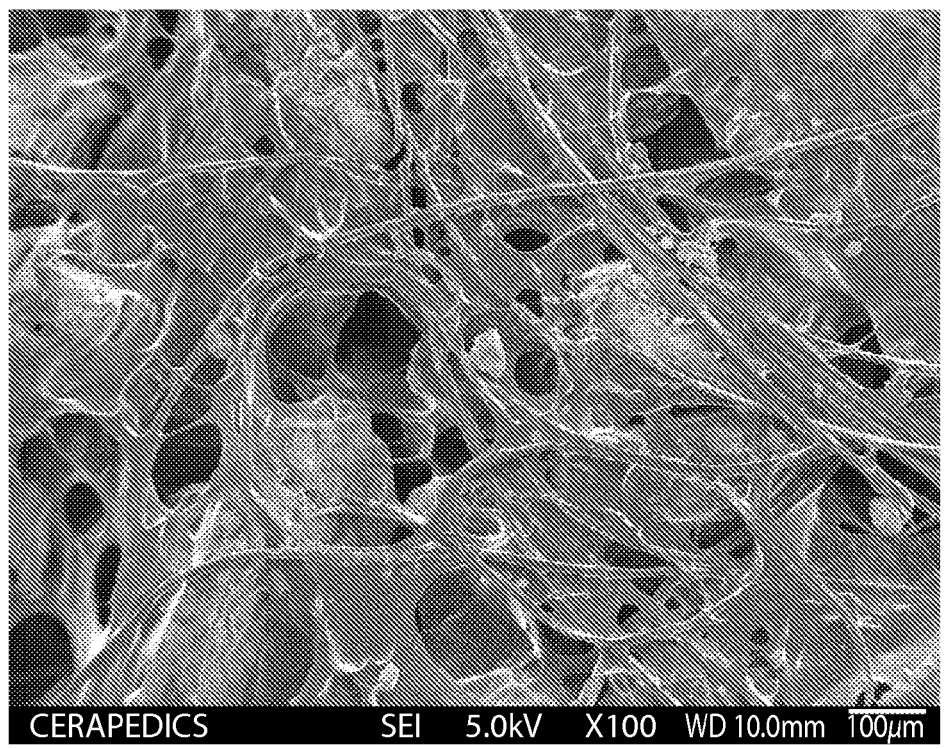
Figure 6B:
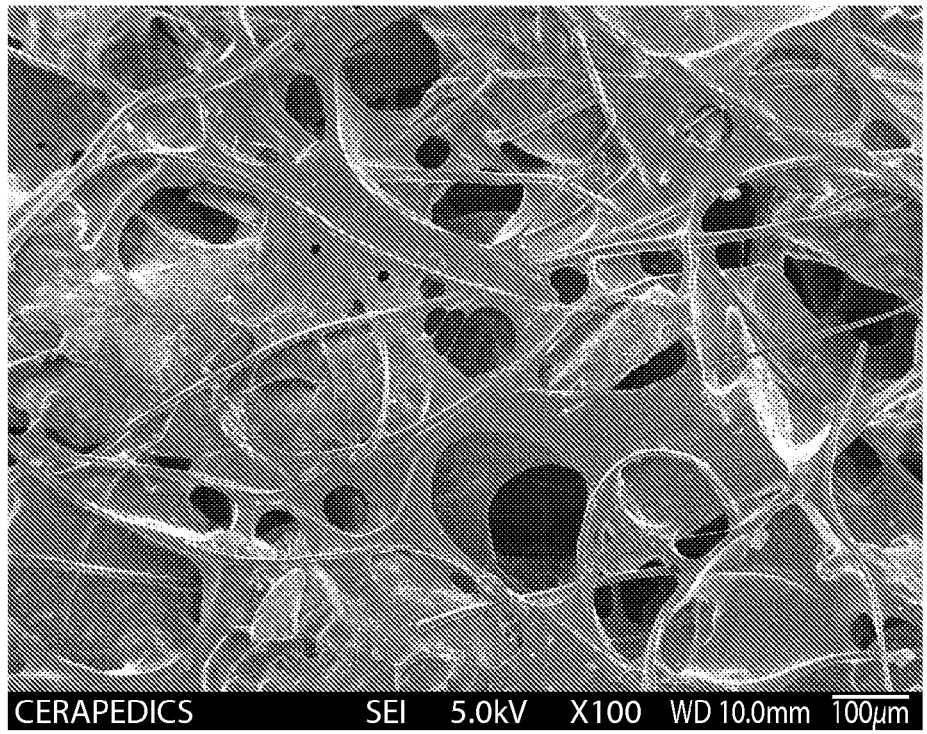

FIGS. 6A and 6B are scanning electron microscopy images of silk fiber reinforced Flex formulations. Mean pore diameter was measured in three separate fields of view for two samples of silk fiber reinforced Flex. In the first sample the mean pore diameter was 96±69 microns. In the second sample the mean pore diameter was 59±31 microns (see Example 11). The SEM images show the interaction of fibers with the lyophilized hydrogel matrix in the formulations of the invention. This type of interaction is believed to enhance the strength of the formulations and reduce particle migration.

Figure 7:
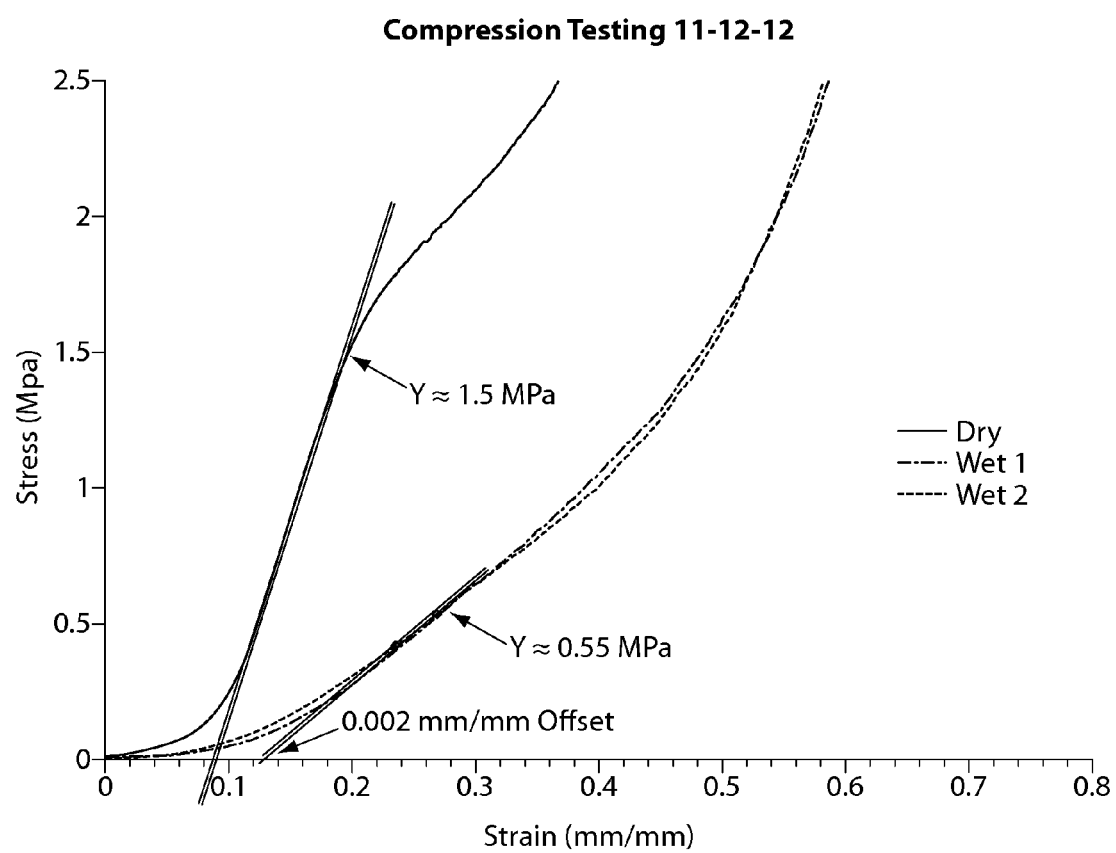

FIG. 7 is a plot of compressive stress versus strain in wet and dry 1.0% silk fiber reinforced Flex formulations (see Example 12). The estimated yield strength (0.2% strain offset) of both dry and wet samples was found to be 1.5 MPa and 0.55 MPa, respectively (n=1, 2).

DETAILED DESCRIPTION

The invention features fiber reinforced bone repair putties and fiber reinforced pliable lyophilized implants which are useful for the treatment of bone defects. The putties and lyophilized implants include ceramic particles suspended in a hydrogel carrier, and include a quantity of fibers. The fiber reinforced formulations of the invention can exhibit reduced migration of the ceramic particles, and are mechanically strengthened so the materials can be aggressively manipulated by a physician during an implantation procedure without tearing or puncturing.

Fibers

The formulations of the invention include fibers having a length from about 0.5 mm to about 15 mm. The fibers can be, without limitation, selected from silk fibers (e.g., textile silk or surgical silk), cellulose fibers, nylon fibers, collagen fibers, elastin fibers, gelatin fibers, keratin fibers, hyaluronan fibers, alginate fibers, glyco-lactide fibers, chitosan fibers, polyethylene fibers, polyurethane fibers, polyglycolide fibers, poly-l-lactide fibers, poly-β-hydroxybutyric acid fibers, polydioxanone fibers, polyester fibers (e.g., PLLA, PGA, PLG, PCL, PMA, PET, and PLA), polycarbonate fibers, dacron fibers, bio-active glass fibers, gold fibers, carbon fibers, nitinol fibers, and stainless steel fibers.

For example, fibers that can be used in the formulations of the invention include, without limitation, resorbable fibers, such as homopolymers or copolymers of monomers selected from the group consisting of L-lactide, L-lactic acid, D-lactide, D-lactic acid, D,L-lactide, glycolide, α-hydroxybutyric acid, α-hydroxyvaleric acid, α-hydroxyacetic acid, α-hydroxycaproic acid, α-hydroxyheptanoic acid, α-hydroxydecanoic acid, α-hydroxymyristic acid, α-hydroxyoctanoic acid, α-hydroxystearic acid, hydroxybutyrate, hydroxyvalerate, β-propiolactide, α-propiolactic acid, γ-caprolactone, β-caprolactone, γ-butyrolactone, pivalolactone, tetramethylglycolide, tetramethylglycolic acid, dimethylglycolic acid, trimethylene carbonate, and dioxanone; peptide fibers, such as silk, collagen, and keratins; polysaccharide fibers, such as cellulose, chitin and chitosan; and mixtures thereof. Alternatively, the fibers used in the formulations of the invention can be inorganic fibers, such as bio-active glass fibers, gold fibers, carbon fibers, nitinol fibers, and stainless steel fibers.

The fibers used in the formulations of the invention can have an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm), and an average diameter of from 5 μm to 60 μm (e.g., from 5 μm to 20 μm, 15 μm to 30 μm, 20 μm to 40 μm, or 35 μm to 60 μm).

Fibers Including Cell Adhesion Peptides

The fibers in the formulations of the invention optionally include one or more cell adhesion peptides. Cell adhesion peptides can include any of the proteins of the extracellular matrix which are known to play a role in cell adhesion, including fibronectin, vitronectin, laminin, elastin, fibrinogen, and collagens, such as types I, II, and V, as well as their bioactive fragments. Additionally, the cell adhesion peptides may be any peptide derived from any of the aforementioned proteins, including derivatives or fragments containing the binding domains of the above-described molecules. Exemplary peptides include those having integrin-binding motifs, such as the RGD (arginine-glycine-aspartate) motif, the YIGSR (SEQ ID NO: 21) (tyrosine-isoleucine-glycine-serine-arginine) motif, and related peptides that are functional equivalents. For example, peptides containing RGD sequences (e.g., GRGDS) (SEQ ID NO: 22) and WQPPRARI (SEQ ID NO: 23) sequences are known to direct spreading and migrational properties of endothelial cells (see V. Gauvreau et al., Bioconjug Chem. 16:1088 (2005)). REDV (SEQ ID NO: 24) tetrapeptide has been shown to support endothelial cell adhesion but not that of smooth muscle cells, fibroblasts, or platelets, and YIGSR (SEQ ID NO: 21) pentapeptide has been shown to promote epithelial cell attachment, but not platelet adhesion (see Boateng et al., Am. J. Physiol. Cell Physiol. 288:30 (2005). Other examples of cell-adhesive sequences are the NGR tripeptide, which binds to CD13 of endothelial cells (see L. Holle et al., Oncol. Rep. 11:613 (2004)) and DGEA (SEQ ID NO: 14) that binds Type I collagen (see Hennessy et. al. Biomaterials, 30:1898 (2009)).

Cell adhesion peptides that can be used in the implantable compositions of the invention include, without limitation, those mentioned above, and the peptides disclosed in U.S. Pat. No. 6,156,572; U.S. patent publication No. 2003/0087111; and U.S. patent publication No. 2006/0067909, each of which is incorporated herein by reference.

In certain embodiments, the cell adhesion peptide is a collagen mimetic peptide. The integrin α2β1 consists of two non-identical subunits, α2 and β1, members of the integrin family each with a single trans-membrane domain, and α2β1 is known to bind to collagen via a specialized region of the α2-subunit. There are several known α2β1 recognition sites within collagens. This knowledge arises from the use of collagen fragments derived from purified α chains cleaved into specific and reproducible peptides. Collagen mimetic peptides that can be used in the implantable compositions of the invention include, without limitation, those described in PCT Publication Nos. WO/1999/050281; WO/2007/017671; and WO/2007/052067, each of which is incorporated herein by reference. Collagen mimetic peptides include, without limitation, peptides including the peptide sequences of any of SEQ ID NOS. 1-20: Gly-Thr-Pro-Gly-Pro-Gln-Gly-Ile-Ala-Gly-Gln-Arg-Gly-Val-Val (SEQ ID NO. 1, also known as "P-15"), Gly-Pro-Gln-Gly-Ile-Ala-Gly-Gln-Arg (SEQ ID NO: 2), Gln-Gly-Ile-Ala-Gly-Gln (SEQ ID NO: 3), Gln-Gly-Ile-Ala-Gly-Gln-Arg (SEQ ID NO: 4), Phe-Gly-Ile-Ala-Gly-Phe (SEQ ID NO: 5), Gly-Ile-Ala-Gly-Gln (SEQ ID NO: 6), Gln-Gly-Ala-Ile-Ala-Gln (SEQ ID NO: 7), Phe-Gly-Ile-Ala-Gly-Phe (SEQ ID NO:8), Cys-Gly-Ile-Ala-Gly-Cys (SEQ ID NO:9), Glu-Gly-Ile-Ala-Gly-Lys (SEQ ID NO:10), N-Acetyl Ile-Ala-Ala (SEQ ID NO:11), Ile-Ala-.beta.Ala (SEQ ID NO:12), N-Acetyl Ile-Ala NMe (SEQ ID NO:13), Asp-Gly-Glu-Ala (SEQ ID NO:14), Asp-Gly-Glu-Ala-Gly-Cys (SEQ ID NO:15), Gly-Phe-Pro*-Gly-Glu-Arg (SEQ ID NO:16, where Pro*=hydroxyproline), Gly-Leu-Pro*-Gly-Glu-Arg (SEQ ID NO:17, where Pro*=hydroxyproline), Gly-Met-Pro*-Gly-Glu-Arg (SEQ ID NO:18, where Pro*=hydroxyproline), Gly-Ala-Ser-Gly-Glu-Arg (SEQ ID NO:19), Gly-Leu-Ser-Gly-Glu-Arg (SEQ ID NO:19), Gly-Ala-Pro*-Gly-Glu-Arg (SEQ ID NO:20, where Pro*=hydroxyproline), and any other collagen mimetic peptides described in U.S. Pat. No. 7,199,103, incorporated herein by reference.

For example, the cell adhesion peptide can be conjugated to the fibers. For example, silk fibers can be modified by covalent coupling to cell adhesion peptides using methods previously described by Chen et al., J Biomed Mater Res A. 67:559 (2003). Briefly, the carboxyl groups of aspartatic acid and glutamic acid amino acids in the silk fibers can be activated (i.e., by reaction with 1-ethyl-3-dimethylaminopropyl carbodiimide hydrochloride (EDC) and N-hydroxysuccinimide (NHS)) in PBS, and then reacted with the N-terminus of the cell adhesion peptide to produce a fiber including the cell adhesion peptide.

Particulate Bone Graft Substitutes

The formulations of the invention include a particulate bone graft substitute. The bone graft substitute can be a particulate ceramic, for example, selected from calcium phosphate materials, such as mineralized bone matrix, deorganified bone matrix, anorganic bone mineral, or a mixture thereof. The calcium phosphate may be any biocompatible, calcium phosphate material known in the art. The calcium phosphate material may be produced by any one of a variety of methods and using any suitable starting components. For example, the calcium phosphate material may include amorphous, apatitic calcium phosphate. Calcium phosphate material may be produced by solid-state acid-base reaction of crystalline calcium phosphate reactants to form crystalline hydroxyapatite solids. Other methods of making calcium phosphate materials are known in the art, some of which are described below. Alternatively, the calcium phosphate material can be crystalline hydroxyapatite (HA). Crystalline HA is described, for example, in U.S. Pat. Nos. Re. 33,221 and Re. 33,161. These patents teach preparation of calcium phosphate remineralization compositions and of a finely crystalline, non-ceramic, gradually resorbable hydroxyapatite carrier material based on the same calcium phosphate composition. A similar calcium phosphate system, which consists of tetracalcium phosphate (TTCP) and monocalcium phosphate (MCP) or its monohydrate form (MCPM), is described in U.S. Pat. Nos. 5,053,212 and 5,129,905. This calcium phosphate material is produced by solid-state acid-base reaction of crystalline calcium phosphate reactants to form crystalline hydroxyapatite solids. Carbonate substituted crystalline HA materials (commonly referred to as dahllite) may be prepared (see U.S. Pat. No. 5,962,028). These HA materials (commonly referred to as carbonated hydroxyapatite) can be formed by combining the reactants with an aqueous liquid to provide a substantially uniform mixture, shaping the mixture as appropriate, and allowing the mixture to harden in the presence of water. During hardening, the mixture crystallizes into a solid and essentially monolithic apatitic structure. The reactants will generally include a phosphate source, e.g., phosphoric acid or phosphate salts, an alkali earth metal, particularly calcium, optionally crystalline nuclei, particularly hydroxyapatite or calcium phosphate crystals, calcium carbonate, and a physiologically acceptable lubricant. The dry ingredients may be pre-prepared as a mixture and subsequently combined with aqueous liquid ingredients under conditions where substantially uniform mixing occurs.

Cell Adhesion Peptides

The ceramic particles in the formulations of the invention are optionally coated with one or more cell adhesion peptides. Cell adhesion peptides can include any of the proteins of the extracellular matrix which are known to play a role in cell adhesion, including fibronectin, vitronectin, laminin, elastin, fibrinogen, and collagens, such as types I, II, and V, as well as their bioactive fragments. Additionally, the cell adhesion peptides may be any peptide derived from any of the aforementioned proteins, including derivatives or fragments containing the binding domains of the above-described molecules. Exemplary peptides include those having integrin-binding motifs, such as the RGD (arginine-glycine-aspartate) motif, the YIGSR (SEQ ID NO: 21) (tyrosine-isoleucine-glycine-serine-arginine) motif, and related peptides that are functional equivalents. For example, peptides containing RGD sequences (e.g., GRGDS) (SEQ ID NO: 22) and WQPPRARI (SEQ ID NO: 23) sequences are known to direct spreading and migrational properties of endothelial cells (see V. Gauvreau et al., Bioconjug Chem. 16:1088 (2005)). REDV (SEQ ID NO: 24) tetrapeptide has been shown to support endothelial cell adhesion but not that of smooth muscle cells, fibroblasts, or platelets, and YIGSR (SEQ ID NO: 21) pentapeptide has been shown to promote epithelial cell attachment, but not platelet adhesion (see Boateng et al., Am. J. Physiol. Cell Physiol. 288:30 (2005). Other examples of cell-adhesive sequences are the NGR tripeptide, which binds to CD13 of endothelial cells (see L. Holle et al., Oncol. Rep. 11:613 (2004)) and DGEA (SEQ ID NO: 14) that binds Type I collagen (see Hennessy et. al. Biomaterials, 30:1898 (2009)).

Cell adhesion peptides that can be used in the implantable compositions of the invention include, without limitation, those mentioned above, and the peptides disclosed in U.S. Pat. No. 6,156,572; U.S. patent publication No. 2003/0087111; and U.S. patent publication No. 2006/0067909, each of which is incorporated herein by reference.

Alternatively, the cellular adhesion peptides can be obtained by screening peptide libraries for adhesion and selectivity to specific cell types (e.g. endothelial cells) or developed empirically via Phage display technologies.

In certain embodiments, the cell adhesion peptide is a collagen mimetic peptide. The integrin $\alpha 2\beta 1$ consists of two non-identical subunits, $\alpha 2$ and $\beta 1$, members of the integrin family each with a single trans-membrane domain, and $\alpha 2\beta 1$ is known to bind to collagen via a specialised region of the $\alpha 2$-subunit. There are several known $\alpha 2\beta 1$ recognition sites within collagens. This knowledge arises from the use of collagen fragments derived from purified $\alpha$ chains cleaved into specific and reproducible peptides. Collagen mimetic peptides that can be used in the implantable compositions of the invention include, without limitation, those described in PCT Publication Nos. WO/1999/050281; WO/2007/017671; and WO/2007/052067, each of which is incorporated herein by reference. Collagen mimetic peptides include, without limitation, peptides including the peptide sequences of any of SEQ ID NOS. 1-20: Gly-Thr-Pro-Gly-Pro-Gln-Gly-Ile-Ala-Gly-Gln-Arg-Gly-Val-Val (SEQ ID NO. 1, also known as "P-15"), Gly-Pro-Gln-Gly-Ile-Ala-Gly-Gln-Arg (SEQ ID NO: 2), Gln-Gly-Ile-Ala-Gly-Gln (SEQ ID NO: 3), Gln-Gly-Ile-Ala-Gly-Gln-Arg (SEQ ID NO: 4), Phe-Gly-Ile-Ala-Gly-Phe (SEQ ID NO: 5), Gly-Ile-Ala-Gly-Gln (SEQ ID NO: 6), Gln-Gly-Ala-Ile-Ala-Gln (SEQ ID NO: 7), Phe-Gly-Ile-Ala-Gly-Phe (SEQ ID NO:8), Cys-Gly-Ile-Ala-Gly-Cys (SEQ ID NO:9), Glu-Gly-Ile-Ala-Gly-Lys (SEQ ID NO:10), N-Acetyl Ile-Ala-Ala (SEQ ID NO:11), Ile-Ala-.beta.Ala (SEQ ID NO:12), N-Acetyl Ile-Ala NMe (SEQ ID NO:13), Asp-Gly-Glu-Ala (SEQ ID NO:14), Asp-Gly-Glu-Ala-Gly-Cys (SEQ ID NO:15), Gly-Phe-Pro*-Gly-Glu-Arg (SEQ ID NO:16, where Pro*=hydroxyproline), Gly-Leu-Pro*-Gly-Glu-Arg (SEQ ID NO:17, where Pro*=hydroxyproline), Gly-Met-Pro*-Gly-Glu-Arg (SEQ ID NO:18, where Pro*=hydroxyproline), Gly-Ala-Ser-Gly-Glu-Arg (SEQ ID NO:19), Gly-Leu-Ser-Gly-Glu-Arg (SEQ ID NO:19), Gly-Ala-Pro*-Gly-Glu-Arg (SEQ ID NO:20, where Pro*=hydroxyproline), and any other collagen mimetic peptides described in U.S. Pat. No. 7,199,103, incorporated herein by reference.

For example, the cell adhesion peptide can be coated onto ABM particles have a mean particle diameter of 300 microns, and nearly all will fall within a range between 200 microns to 425 microns. However, a particle size range between 50 microns to 2000 microns may also be used.

Anorganic bone mineral (ABM) may also be a synthetic alloplast matrix or some other type of xenograft or allograft mineralized matrix that might not fit the definition of "anorganic." The alloplast could be a calcium phosphate material or it could be one of several other inorganic materials that have been used previously in bone graft substitute formulations, e.g., calcium carbonates, calcium sulphates, calcium silicates, used in a mixture that includes calcium phosphate and that could function as biocompatible, osteoconductive matrices. The anorganic bone mineral, synthetic alloplast matrix, and xenograft or allograft mineralized matrix are can be the particulate bone graft substitute and can be used to bind a cell adhesion peptide to their surface.

Hydrogels

To prepare a fiber reinforced putty of the invention, the particulate bone graft substitute can be suspended in a biocompatible polysaccharide gel along with short fibers. Polysaccharides that may be utilized include, for example, any suitable polysaccharide within the following classes of polysaccharides: celluloses/starch, chitin and chitosan, hyaluronic acid, alginates, carrageenans, agar, and agarose. Certain specific polysaccharides that can be used include agar methylcellulose, hydroxypropyl methylcellulose, carboxymethylcellulose, ethylcellulose, microcrystalline cellulose, oxidized cellulose, chitin, chitosan, alginic acid, sodium alginate, and xanthan gum.

The hydrogels will typically include a solvent to control the viscosity of the material. The solvent may be an alcohol or alcohol ester, including for example, glycerol, triacetin, isopropyl alcohol, ethanol, and ethylene glycol, or mixtures of these. The paste or gel can include others components, such as surfactants, stabilizers, pH buffers, and other additives (e.g., growth factors, antibiotics, analgesics, etc.). For example, a suitable gel or paste can be prepared using water, glycerin and sodium carboxymethylcellulose.

The pliable lyophilized fiber reinforced implants (i.e., the Flex materials) are prepared, as described in Example 1, by lyophilization of a fiber reinforced putty.

Therapy

The compositions of the invention can be used as bone graft substitutes which are implanted into a subject. The compositions of the invention can include a cell adhesion peptide to promote rapid ossification of the implant.

The compositions of the invention can be useful for repairing a variety of orthopedic conditions. For example, the compositions may be injected into the vertebral body for prevention or treatment of spinal fractures, injected into long bone or flat bone fractures to augment the fracture repair or to stabilize the fractured fragments, or injected into intact osteoporotic bones to improve bone strength. The compositions can be useful in the augmentation of a bone-screw or bone-implant interface. Additionally, the compositions can be useful as bone filler in areas of the skeleton where bone may be deficient. Examples of situations where such deficiencies may exist include post-trauma with segmental bone loss, post-bone tumor surgery where bone has been excised, and after total joint arthroplasty (e.g., impaction grafting and so on). The compositions may be formulated as a paste prior to implantation to hold and fix artificial joint components in patients undergoing joint arthroplasty, as a strut to stabilize the anterior column of the spine after excision surgery, as a structural support for segmented bone (e.g., to assemble bone segments and support screws, external plates, and related internal fixation hardware), and as a bone graft substitute in spinal fusions.

The compositions of the invention can be used to coat prosthetic bone implants. For example, where the prosthetic bone implant has a porous surface, the composition may be applied to the surface to promote bone growth therein (i.e., bone ingrowth). The composition may also be applied to a prosthetic bone implant to enhance fixation within the bone.

The compositions of the invention can be used as a remodeling implant or prosthetic bone replacement, for example in orthopedic surgery, including hip revisions, replacement of bone loss, e.g. in traumatology, remodeling in maxillofacial surgery or filling periodontal defects and tooth extraction sockets, including ridge augmentation and sinus elevation. The compositions of the invention may thus be used for correcting any number of bone deficiencies at a bone repair site.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention

EXAMPLE 1

Preparation of Fiber-Reinforced Implantable Materials

A fiber reinforced putty and fiber reinforced Flex (lyophilized putty) were prepared using methods analogous to those described in PCT Publication No. WO2007070681.

Preparation of Putty

A putty material containing about 51.9% (w/w) anorganic bone mineral particles (ABM, a natural microporous, xenogenic bone material also known as OsteoGraf®-N 300); about 1.5% (w/w) sodium carboxymethyl cellulose; about 6.98% (w/w) glycerol; and about 39.57% (w/w) water was prepared mixing the water, glycerol, and sodium carboxymethyl cellulose to form a hydrogel, and mixing the ABM particles with the hydrogel to form a putty. The hydrogel/putty is optionally subjected to a vacuum to remove any air bubbles formed during mixing. The ABM particles optionally include P-15 peptide (see U.S. Pat. No. 5,635,482) bound to their surface (sold as PEPGEN P-15® by Dentsply Tulsa Dental Specialties).

Preparation of Fiber-reinforced Putty

To the above putty was added a predetermined quantity of fibers in small increments with mixing. A homogeneous batch was achieved by using a mixing device, such as a Ross double planetary mixer fitted with blades, such as the Ross, high viscosity (HV) blades.

Preparation of Fiber-reinforced Flex

The fiber reinforced putty was shaped (i.e., in a mold), placed in a low-temperature freezer (−65° C.) for no less than one hour, and lyophilized for at least 5 hours. The water content of the resulting fiber reinforced Flex material can be assessed following exposure to ambient air. The water content may be adjusted by exposure to moisture, or drying conditions, as needed.

The fiber-reinforced Flex formulations described in the examples are identified by the weight percent of fiber included in the putty lyophilized to form the Flex formulation. The approximate weight percentage of fiber in the resulting Flex formulations is higher following removal of water from the putty. The approximate fiber content of the Flex formulations is provided in Table 1 below.

TABLE 1

| Flex product | Fiber content in the Putty formulation | Range of fiber content in Flex formulation[1] |
|---|---|---|
| Flex | 0 | 0 |
| 0.25% Flex | 0.25% (w/w) | 0.38% to 0.41% (w/w) |
| 0.5% Flex | 0.5% (w/w) | 0.77% to 0.82% (w/w) |
| 1% Flex | 1.0% (w/w) | 1.54% to 1.64% (w/w) |
| 2% Flex | 2.0% (w/w) | 2.99% to 3.19% (w/w) |

[1]Calculated concentration assuming from 1% to 7% water content in the Flex formulation.

EXAMPLE 2

The Modified Ball Punch Deformation Test

The fiber reinforced Flex can improve ease of handling and implantation by a surgeon in comparison to fiberless formulations. The fiber reinforced materials can also reduce particle migration post implantation.

A tensile test, which is the standard mechanical test for current Flex product, cannot properly test the material in a real-world scenario since the product is rarely pulled apart. Rather, during implantation of the lyophilized formulations, manual pressure is applied to strips of Flex in a puncturing motion, not pulling. To ascertain the performance of the product under realistic surgical conditions, an ideal test would also be performed on both dry and wetted (using various techniques and fluids) Flex samples.

To assess whether a fiber reinforced Flex can better withstand manual puncturing motion, a new testing method, the Modified Ball Punch Deformation Test (BPD test), was developed. The BPD test mimics real-world handling characteristics for Flex and fiber reinforced Flex products. Further, this test is a modified version of ASTM E643.

Figure 1:
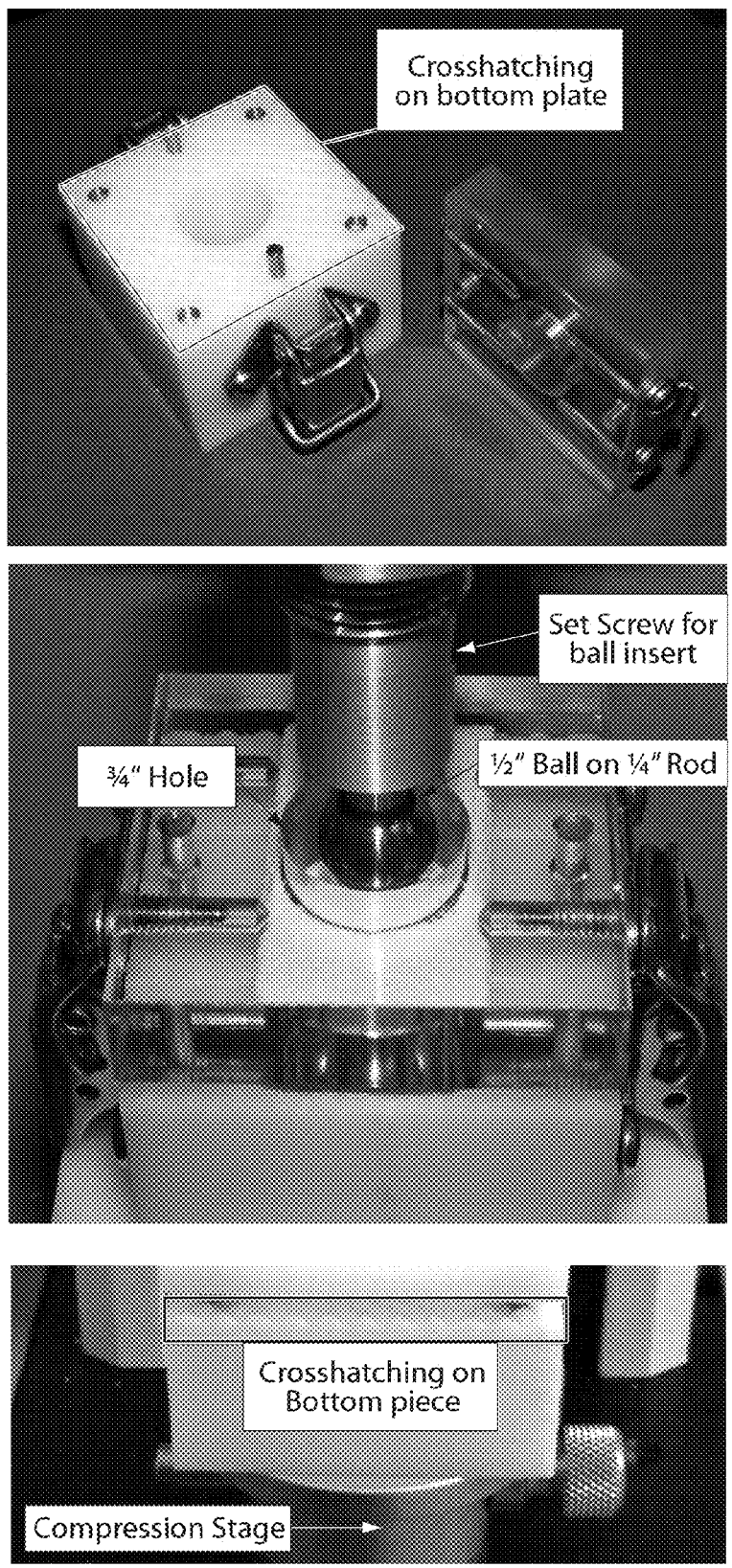
FIG. 1 are pictures of the device used to carry out the Ball Punch Deformation (BPD) test described in Example 2.

A sample of the Flex material is placed in the sample holder of the BPD testing device (see FIG. 1B). The device includes a ½" ball with ¾" die (see FIG. 1A). The sample is aligned over the hole in the bottom die, the top die is aligned over the sample, and the latches are secured to ensure that the sample does not move. A crosshatched base piece also minimizes sample draw-in (pulling in from the sides). The ball is centered over the ¾" hole of the holder, and positioned just above the sample to be tested. The test commences as the ball moves at 0.5 mm/second with a maximum extension of 15 mm from the point of first contact. The compressive load (i.e., the force applied in compression measured in Newtons) is recorded as the ball advances against the sample. The BPD test measures (i) the load at failure (LAF, the maximum load reached before failure of sample), (ii) the extension at failure (EAF, the compressive extension value at maximum load), and (iii) the modulus (i.e., stiffness) of the sample (the slope of the linear region of the BPD test curve plotting compressive load versus compressive extension).

To test the wetted Flex product, the Flex is wetted by submerging the entire assembly of the dry Flex sample positioned in the sample holder in phosphate buffered saline (PBS) for five minutes. The excess liquid is then removed and the sample tested.

Figure 2:
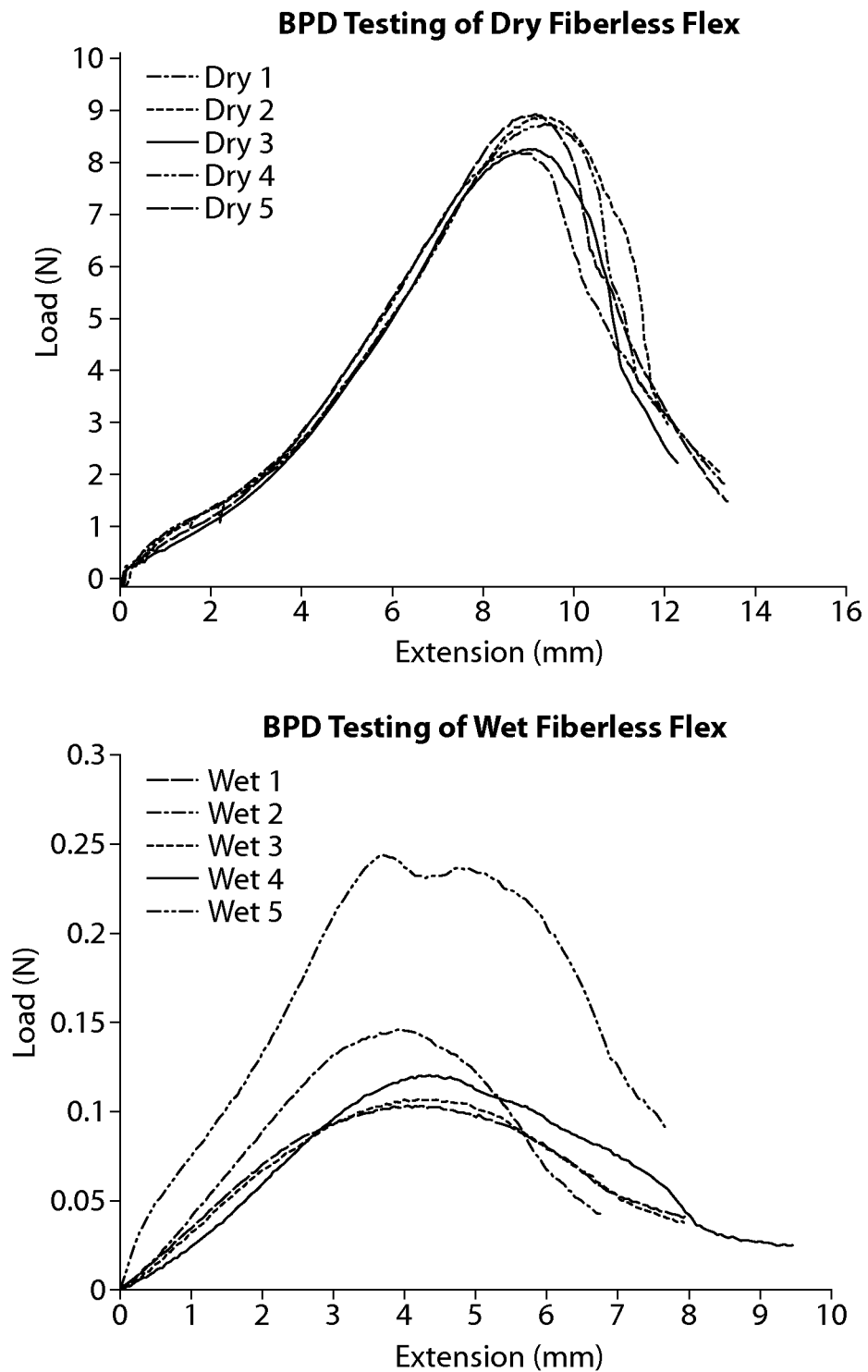
FIG. 2 are graphs plotting the compressive load (N) versus extension (mm) for lyophilized samples tested dry (left) and wet (right) using the BPD test described in Example 2.
Figure 3:
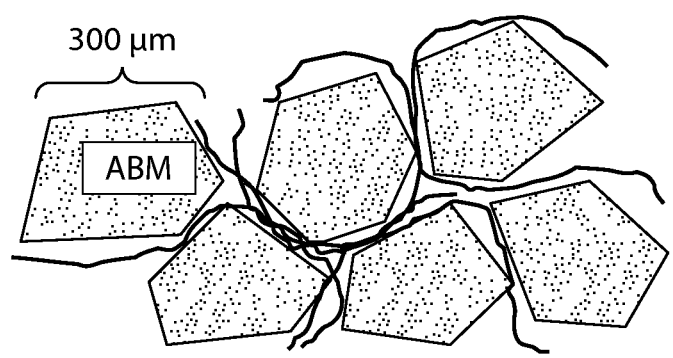
FIG. 3 is a drawing depicting the interaction of fibers with the ceramic particles in the formulations of the invention. This type of interaction (as well as interactions with the carrier matrix) is believed to enhance the strength of the formulations and reduce particle migration.

Exemplary data are shown in FIG. 2. The BPD test results are depicted for fiberless Flex. The test results show good reproducibility for dry material with an average LAF of 8.5 N, and an average EAF of about 9 mm (see FIG. 2 right). In contrast, wet fiberless Flex exhibits an appreciable decrease in LAF (average about 0.15 N), and appreciable decrease in EAF (average about 3.7 mm) (see FIG. 2 left).

EXAMPLE 3

Effect of Silk Fiber Length and Concentration on Mechanical Properties for Fiber Reinforced Flex The purpose of the following study was to understand the effect of silk fiber length and concentration on mechanical properties for silk fiber reinforced Flex (SFR Flex) samples.

SFR Flex samples were prepared using the methods described in Example 1. The fibers used for this study were roving silk fiber (textile grade) cut to ½", ⅜" and ¼" lengths. The samples were subjected to BPD testing as described in Example 2. The results are tabulated below in Table 2.

TABLE 2

| Fiber Length (in) | Fiber Percentage (%) | Testing Environment | Load at Failure (N) |
|---|---|---|---|
| NA | 0 | Dry | 13.53 |
|  |  | Wet | 0.352 |
| ½ | 1.0 | Dry | 55.85 |
|  |  | Wet | 20.794 |
|  | 0.5 | Dry | 42.13 |
|  |  | Wet | 6.294 |
|  | 0.25 | Dry | 32.2 |
|  |  | Wet | 2.395 |
| ⅜ | 1.0 | Dry | 63.09 |
|  |  | Wet | 26.981 |
|  | 0.5 | Dry | 39.83 |
|  |  | Wet | 10.497 |
|  | 0.25 | Dry | 26.07 |
|  |  | Wet | 5.435 |
| ¼ | 1.0 | Dry | 50.49 |
|  |  | Wet | 9.457 |
|  | 0.5 | Dry | 22.12 |
|  |  | Wet | 3.658 |
|  | 0.25 | Dry | 21.43 |
|  |  | Wet | 2.753 |

Results and Discussion:

A steady decrease in LAF can be observed as fiber content decreases, the lowest LAF values generally being observed in fiberless Flex samples. The dry 1.0% SFR Flex samples exhibit LAF values as high as five times larger than dry fiberless Flex. All dry 0.5% SFR Flex samples are stronger than dry fiberless Flex with LAF values from over two to almost four times larger. The dry 0.25% SFR Flex samples are around two times stronger than dry fiberless Flex.

The modulus of dry 1% SFR Flex samples were observed to be similar, but in dry 0.5% SFR Flex and dry 0.25% SFR Flex samples the modulus begins to decrease indicating a lower stiffness in those samples. This can be qualitatively felt between samples. On average, 1.0% SFR Flex samples were stiffer in comparison to all others. They maintained torsion flexibility but were much stiffer in tension. This is most likely due to increased internal frictional force between the fibers and the ABM particles. Upon wetting, the 1.0% SFR Flex samples were still very cohesive and required a large force to manually pull apart. The 0.5% SFR Flex and 0.25% SFR Flex samples were more flexible and behaved very similarly to fiberless Flex. They were noticeably stronger and took more force to break than fiberless Flex. Upon wetting, the samples were still stronger than fiberless Flex but broke fairly easily.

The strength differences observed in the ½" and ⅜" samples may be attributed to the number of fibers found in a given sample. If there are two equal weight piles of fibers with lengths 12 mm and 6 mm, there will be twice as many fibers in the 6 mm pile than the 12 mm. Thus, 1.0% SFR Flex samples with 6 mm fibers will have twice as many fibers as one with 12 mm.

To determine theoretical counts of fibers, silk weight was gathered by taking a small clump of fibers and weighing them. The clump was then placed on a microscope slide, frayed out to separate all individual fibers, taped down and counted. The weight was divided by the number of fibers and then divided by the fiber length to get an overall weight per length of silk. For example, if a clump of 9 mm fibers weighs 0.0018 g and is found to contain 100 fibers, then the weight per mm of fiber is 0.0018 g/(100 fibers*9 mm)=0.000002 g/mm of fiber.

We calculate that for the ⅜" fiber samples (i) there are approximately 11,300 more fibers in the 1.0% SFR Flex sample than the 0.25% SFR Flex sample; (ii) there are approximately 2,800 more fibers in the ⅜" 1.0% SFR Flex sample than ½" 1.0% SFR Flex sample; and (iii) there are approximately 33% more fibers in the ⅜" 1.0% SFR Flex sample that may contribute to the higher observed LAF in these materials.

The mechanism by which the silk fibers strengthen the samples may arise from an abrasive action between the fibers and the ABM particles. The silk fibers may be closely associated with the ABM particles, rather than with the hydrogel carrier. During BPD testing, as the sample begins to deform, silk fibers are pulling away from ABM particulate until the fibers break away and the sample fails. Evidence of this strengthening mechanism can be seen in FIG. 5. The modulus of both the ½" and ¼" SFR Flex samples is very similar (if not the same) until the break-point which occurs as the fibers finally release from between the last ABM particles. The ¼" samples break, on average, 1 mm before the ½" samples. Using the average 300 μm (3 mm) diameter of ABM particles, there are approximately forty (40) and twenty (20) potential particles interacting with the ½" and ¼" silk fibers, respectively (12 mm/0.3 mm=40). Multiple fibers may also be interacting with a single ABM particle.

We calculated that for the 1.0% SFR putty and Flex formulations containing 9 mm length silk fibers, the number ratio of ABM particles to fibers in the formulations is approximately 1:1. This ratio, and the length of the fibers relative to the particle size, can be important in determining the handling characteristics and resistance to migration post implantation for the formulations of the invention.

EXAMPLE 4

In-vitro Simulated PLF Surgery

A simulated Posterolateral Fusion (PLF) using a spine model and sponges was used to correlate qualitative handling characteristic data to quantitative mechanical testing data for Silk Fiber Reinforced (SFR) Flex samples.

SFR Flex samples were prepared using the methods described in Example 1. The fibers used for this study were roving silk fiber (textile grade) cut to ⅜" lengths. 1% SFR Flex, 0.5% SFR Flex, 0.25% SFR Flex, and fiberless Flex samples were used in this study.

Sponge/Spine Model Simulation:

A large sponge was cut in half like a bun, leaving a small portion attached on one side. Zip ties were then pushed through the sponge in the interior center of the bun. A model of the transverse processes of the lumbar spine model were then put inside the bun. The samples were positioned in the sponge model across the inter-transverse process region. Manual pressure was applied to each sample in a worst-case scenario (i.e., much more pressure was used than in a manner consistent with normal surgery). The samples were taken out, stretched, and repositioned numerous times. After initial handling observations, samples were molded into putty-like form and repositioned in the spine.

Handling Observations:

Fiberless Flex samples were very stretchy and flexible in both torsion and tension. At the first positioning of a fiberless Flex sample in the inter-transverse process region, the sample tore and further ripping occurred with minor manual pressure. The fiberless Flex sample began falling apart shortly after hydration and also started turning into putty. More ABM/P-15 particles were observed to flake off (called particulation) of fiberless Flex samples than the SFR Flex samples.

The 0.25% SFR Flex samples were flexible and stretchy in dry form (this formulation felt like fiberless Flex). Once hydrated the formulation became slimy, and also particulated like fiberless Flex. A small tear formed after rigorous manual pressure, once it formed the sample began to fall apart fairly easily. With hydration this formulation formed an SFR Putty.

The 0.5% SFR Flex samples were acceptably flexible, but less flexible that fiberless Flex and 0.25% SFR Flex samples. The 0.5% SFR Flex sample initially ripped upon the first applied pressure, but this did not seem to weaken the strip at all. Subsequent forming yielded no more failures. The 0.5% SFR Flex sample, once hydrated, can be formed back into SFR Putty, reshaped, and reimplanted.

The 1.0% SFR Flex samples were much more stiff in tension, but still maintained their torsion flexibility. This formulation did not initially conform to void spaces when dry. However, wetting the formulation made the strip much more flexible and the strips shaped nicely. The 1.0% SFR Flex sample finally broke after wetting under a large manual tensile force.

This study addresses two important mechanical properties of the reinforced Flex materials: formability and strength. Strength is a vital characteristic in understanding how an implantable material will hold up to manual pressure during surgery. Formability is also very important. For example, the 1.0% SFR Flex sample was very stiff and did not conform very well to the void space initially. Once wet, the sample became more pliable and moldable. It has 50% more strength than the 0.5% SFR Flex sample, but the 0.5% SFR Flex sample had initial formability and enough strength to handle the manual pressure (which was in excess of what would normally be applied during implantation).

Furthermore, reducing the fiber content can result in a product more easily extruded, and simplify mixing procedures in the manufacturing. We have observed that at about the fiber content found in the 0.5% SFR Flex, the putty begins to become more cohesive which leads to harder mixing and less easily extruded for forming operations. The 0.5% SFR Flex containing ⅜" fibers handles well, mixes well, and exhibits properties similar to dry fiberless Flex, whether it itself is dry or wet.

EXAMPLE 5

Effect of Fiber Type and Fiber Diameter on Mechanical Properties

The purpose of this study was to understand the effect of fiber type on mechanical properties of fiber reinforced (FR) Flex.

FR Flex samples were prepared using the methods described in Example 1. The fibers used for this study were fibers of PLLA, PGA and silk (textile and medical) with fiber lengths of 12 mm and 6 mm. Spooled silk was wound, measured and cut to 12 mm lengths manually. Fiber diameter measurements were also taken. The dry samples were subjected to BPD testing as described in Example 2. The results are tabulated below in Table 3.

TABLE 3

Mechanical performance of dry samples.

| Sample | Fiber Type | Fiber Length (mm) | Load at Failure (N) |
|---|---|---|---|
| 1.0% FR Flex | Medical Silk | 12 | 17.6 |
| 0.5% FR Flex | Medical Silk | 12 | 19.2 |
| 1.0% FR Flex | Textile Silk | 12 | 55.85 |
| 0.5% FR Flex | Textile Silk | 12 | 42.13 |
| 0.25% FR Flex | Textile Silk | 12 | 32.12 |
| 1.0% FR Flex | Textile Silk | 6 | 50.49 |
| 0.5% FR Flex | Textile Silk | 6 | 22.12 |
| 0.25% FR Flex | Textile Silk | 6 | 21.43 |
| 0.5% FR Flex | PLLA | 12 | 20.9 |
| 0.5% FR Flex | PGA | 12 | 24.0 |
| Fiberless Flex | NA | 0 | 13.53 |

Results and Discussion:

Medical Silk, PGA and PLLA samples of 0.5% FR Flex show similar LAF values of 19.2, 24.0 and 20.9 N, respectively, and perform more similarly to 6 mm textile silk than to 12 mm textile silk. These samples are all over 1.5 times stronger than fiberless Flex.

We observed that in the textile silk in the 0.5% SFR Flex sample, the sample with the highest LAF, there are three or more times as many fibers present than in any other sample. Surprisingly, this 0.5% SFR Flex sample (containing medical silk) has comparable strength to the 0.5% FR Flex made using PLLA and PGA, though these samples contain 5 and 7.7 times the number of fibers, respectively.

Microscopic images of the fibers were taken, and their diameters were measured. We observed that the PLLA and PGA fibers are much smoother than the medical silk or textile silk. We also observed that the medical grade silk has a much larger diameter than all the other fibers, including the textile silk.

This smoother fibers observed for PLLA and PGA could decrease friction between the ABM particles and the fibers.

Moreover, PLLA and PGA are both more hydrophilic than silk. Therefore, it is hypothesized that the hydrogel could form a lubricating layer around the PLLA and PGA fibers, reducing the friction among ABM particles sliding along the fibers, and reducing the LAF observed for these formulations.

The larger diameter, medical grade silk may not be as strong at the same weight percentage textile silk because there are so few fibers for frictional interactions. The larger fibers are also more rigid and do not form around void spaces like the much smaller textile silk. Therefore, the medical silk simply slides past ABM particles without adding much additional strength. The medical grade silk seems to be a composite of multiple silk fibers and some sort of "glue", possibly sericin or a wax.

EXAMPLE 6

Effect of Fiber on Migration Properties

The purpose of this study was to understand the effect of silk fiber reinforced (SFR) Putty on particulate migration post implantation. With hydration in vivo, the Flex materials form a putty. It is important for the implant to retain the ABM particles at the site of the bone defect.

Fiber reinforced putty samples were prepared using the methods described in Example 1.

An in-vitro model was developed to mimic the cavity in a spinal implant cage and the cage's inserter hole (see FIG. 4A). A middle plate is placed on the bottom plate and Putty is tightly packed into the center cavity. The top plate is then secured using the four screws, sealing the internal cage cavity. A small needle was used to fill the fluid inlet holes with fluid to eliminate air bubbles. Two syringes were filled with phosphate buffered saline (PBS) and attached to a dual-syringe pump set to a rate of 100 μl/minute (200 μl/minute total with both). Tubes connect the syringe and spine cage model via the fluid inlets. A stopwatch was used to measure time from the start of the pump to visible migration of ABM granules that reach the top of the top plate and to measure all other pertinent time points. The results are provided in Table 4.

TABLE 4

| Putty | Fiber | Fiber Length (mm) | Extrusion Time (minutes)[a] |
|---|---|---|---|
| 1.0 wt % SFR Putty | Textile Silk | 9 | 7.5 |
| 0.5 wt % SFR Putty | Textile Silk | 9 | 5.5 |
| Fiberless Putty | NA | 0 | 2.5 |

[a]The amount of time required for the ABM/P-15 particulate to reach the top of the "inserter hole"

Results and Discussion:

The fiberless Putty was the quickest to extrude from the model internal cage cavity at 2.5 minutes (see FIG. 4B). At nine minutes, the pump was turned off because a large "snake" of Putty had extruded from the hole and PBS was beginning to flow out. Approximately 0.4 cc of Putty extruded during this experiment.

At 5.5 minutes the 0.5% SFR Putty began to extrude from the model internal cage cavity (see FIG. 4C). At the end of the test (12 minutes), approximately 0.05 cc of 0.5% SFR Putty had extruded. The majority of the extruded material (ca. 60%) was hydrogel carrier, and not ABM particles.

At 7.5 minutes the 1.0% SFR Putty began to extrude from the model internal cage cavity (see FIG. 4D). At the end of the test (16 minutes), approximately 0.05 cc of 1.0% SFR Putty had extruded. The majority of the extruded material (ca. 80%) was hydrogel carrier and not ABM particles.

The FR Putty materials were found to exhibit a dramatic reduction in their ability to extrude from the site of implantation in comparison to the fiberless formulation.

EXAMPLE 7

Effect of Fiber on the Tensile Strength of the Putty Formulations

The purpose of this study was to understand the effect of silk fiber on the tensile strength of the putty formulations.

Both fiberless and silk fiber reinforced (1% fiber) putty samples were prepared using the methods described in Example 1. Putty formulations were stretched to failure using an Instron™ mechanical testing instrument. As the putty formulation is pulled apart by the instrument, the force exerted by the instrument on the sample was measured, and the yield stress was calculated.

The yield stress (the force per unit area applied to a sample during a mechanical testing) was measured for both the fiberless formulation and the 1% SFR formulation. The fiberless putty exhibited an average yield stress of 5±1 kPa, while the SFR formulation exhibited an average yield stress of 21±2 kPa. The results show that on average the yield stress of the putty increased four fold with the addition of the silk fibers.

EXAMPLE 8

Effect of Fiber on the Tensile Strength of the Flex Formulations

The purpose of this study was to understand the effect of silk fiber on the tensile strength of the Flex formulations.

Both fiberless Flex and 1.0% SFR Flex samples were prepared using the methods described in Example 1. Flex formulations were stretched to failure using an Instron™ mechanical testing instrument. As the Flex formulation is pulled apart by the instrument, the force exerted by the instrument on the sample was measured, and the modulus and yield stress were calculated.

The yield stress and modulus were measured for both the fiberless Flex formulation and the 1% SFR Flex formulation. The results are provided in Table 5.

TABLE 5

| Specimen | Sample Thickness (mm) | Modulus[a] (kPa) | Yield Stress (kPa) |
|---|---|---|---|
| Fiberless Flex | 3.42 | 111 | 41 |
| Fiberless Flex | 3.42 | 90 | 43 |
| Fiberless Flex | 3.44 | 55 | 34 |
| Fiberless Flex | 3.45 | 103 | 40 |
| Fiberless Flex | 3.45 | 97 | 45 |
| Fiberless Flex | 3.44 | 77 | 41 |
| 1% SFR Flex | 3.83 | 2761 | 421 |
| 1% SFR Flex | 3.84 | 2840 | 440 |
| 1% SFR Flex | 3.80 | 3435 | 547 |
| 1% SFR Flex | 3.80 | 2298 | 324 |
| 1% SFR Flex | 3.72 | 1313 | 261 |
| 1% SFR Flex | 3.75 | 1770 | 308 |

[a]Resistance to elastic deformation of a material. It is the ratio of stress to strain in the elastic region of a tensile test. Strain is the change in length of material divided by the original length of the material during mechanical testing.

The fiberless Flex exhibited an average yield stress of 41±3 kPa, while the SFR Flex formulation exhibited an average yield stress of 384±84 kPa. The fiberless Flex exhibited an average modulus of 89±16 kPa, while the SFR formulation Flex exhibited an average modulus of 2,403±458 kPa. The results show that, on average, the yield stress of the Flex increases nine fold and the modulus increases 27 fold with the addition of the silk fibers.

EXAMPLE 9

Effect of Fiber on the LAF and EAF of the Flex Formulations

Both fiberless Flex and 1.0% SFR Flex samples were prepared using the methods described in Example 1. Samples of approximately 4 mm thickness were analyzed using the BPD test described Example 2. The load at failure (LAF) and extension at failure (EAF) results are provided in Table 6.

TABLE 6

| Specimen | Sample Thickness (mm) | Load at Failure (LAF) (N) | Extension at Failure (EAF) (mm) |
| --- | --- | --- | --- |
| Fiberless Flex | 3.60 | 7.92 | 10.05 |
| Fiberless Flex | 3.53 | 6.87 | 10.20 |
| Fiberless Flex | 3.63 | 7.68 | 10.20 |
| Fiberless Flex | 3.71 | 8.05 | 9.85 |
| Fiberless Flex | 3.55 | 8.17 | 10.50 |
| Fiberless Flex | 3.67 | 7.99 | 10.10 |
| 1% SFR Flex | 3.83 | 64.95 | 7.40 |
| 1% SFR Flex | 3.89 | 60.39 | 7.40 |
| 1% SFR Flex | 3.87 | 75.09 | 8.00 |
| 1% SFR Flex | 3.89 | 57.32 | 7.15 |
| 1% SFR Flex | 3.92 | 60.41 | 8.85 |
| 1% SFR Flex | 3.93 | 83.48 | 8.25 |

The fiberless Flex exhibited an average LAF of 7.8±0.4 N and an average EAF of 10.2±0.2 mm. In contrast, the 1% SFR Flex formulation exhibited an LAF of 66.9±8.2 N and an EAF of 7.8±0.5 mm. Some draw-in was observed (i.e., during testing, samples will pull in from the sides of the holder and skew extension data) of fiberless Flex which contribute slightly to their larger EAF values in comparison to those observed for the SFR Flex formulation.

EXAMPLE 10

Migration Characteristics of Flex Formulations in an Animal Model

The purpose of this three week, lumbar spine, pilot study in sheep was to compare product migration characteristics of fiber reinforced Flex formulations to the fiberless Flex formulation. In order to evaluate the migratory effect of Flex formulations on a posterior lumbar interbody fusion (PLIF) procedure, a well-established ovine PLIF model was be utilized. This model has been accepted by researchers, clinicians, and regulators as a predictive model for spine fusion related procedures in humans. The current study was aimed at not only implanting the constructs but further evaluating migration after surgery in live animals. These spine fusion surgeries were performed un-instrumented to ensure maximum mobility of the spine after surgery and before sacrifice. This was intended to provide a worst-case test scenario for each of the samples.

Flex Samples Tested

The following Flex samples were prepared using the methods described in Example 1:
(1) fiberless Flex;
(2) fiber reinforced Flex formed from putty containing 0.5% (w/w) PLLA fibers 12 mm in length;
(3) fiber reinforced Flex formed from putty containing 0.5% (w/w) silk fibers 9 mm in length that were washed with $Na_2CO_3$ to remove 98% of the sericin on the surface of the silk fibers; and
(4) fiber reinforced Flex formed from putty containing 1.0% (w/w) silk fibers 9 mm in length that were washed with $Na_2CO_3$ to remove 98% of the sericin on the surface of the silk fibers.

Three samples of each formulation was tested for water content (Karl Fischer) and percent solids content. The average water content of the fiberless Flex and FR Flex samples was 3.7% and 3.4%, respectively. The average anhydrous percent solids was 86% and 86.4% for the fiberless Flex and FR Flex samples, respectively.

Samples of approximately 3.5 to 4.0 mm thickness were analyzed using the BPD test described Example 2. Upon wetting 1.0% SFR Flex, 0.5% SFR Flex, 0.5% FR Flex containing PLLA fibers, and fiberless Flex lose approximately 59%, 63%, 76%, and 94% of their dry strength, respectively (see FIG. 5). Although silk and PLLA at the same weight percent addition have similar dry LAF values, their wet LAF values are significantly different. This loss indicates a difference in relative cohesion of the strips; silk FR Flex formulations seem to have a higher cohesion than PLLA FR Flex formulations.

Implantation

In brief, six skeletally mature, female sheep each underwent a single-level un-instrumented PLIF procedure. A posterior approach was used to expose the lamina and transverse processes (TP) with dissection made at the L4 to the L5 level at the mid-line along the spinous processes and across the transverse processes to the tips. The facets were removed with a ronguer and the tranverse processes and vertebral bodies were carefully decorticated with a burr. The experimental materials were placed in the gutter of the spine, next to and across the transverse processes of the lumbar vertebral bodies L4 and L5.

A three week end point for testing implant migration was chosen based on the normal stages of wound healing. At 3 weeks post operatively the implant location was expected to be at its permanent location, thus allowing accurate determination of implant migration.

All four Flex formulations were implanted into the lumbar spine of sheep (3 samples each implanted into 6 sheep). Surgical sites for all sheep were very well prepared and kept as dry as possible. During implantation, all samples were set in place and torn to fit (approximately 30 mm torn off). Sheep necropsy and lumbar spine excisions were performed after 3 weeks in-life.

Handling Characteristics

All FR Flex samples were less flexible than fiberless Flex, with the 1.0% SFR Flex formulation being the least flexible of all (tensile elongation was very low, but it was still highly flexible in torsion and bending).

All samples exhibited some particulation at the tear site, and fiberless Flex was crumbling in this region. All fiber reinforced samples were harder to tear than fiberless Flex with 1.0% SFR Flex being the most difficult.

The 0.5% FR Flex with PLLA fibers and 1.0% SFR Flex formulations were not as initially cohesive to the implantation site as fiberless Flex and bounced back. After some hydration, they began to stick to the bone and were more conformable.

Post-Necropsy X-ray, CT and Dissection

Post-necropsy x-rays provided thinning and migrating information at first glance with good resolution. For the three implanted samples a count of samples observed to have thinned or migrated is provided in Table 7.

TABLE 7

| Sample | Thinned | Migrated |
|---|---|---|
| Fiberless Flex | 3 | 1 |
| 0.5% FR Flex (PLLA) | 1 | 1 |
| 0.5% SFR Flex | 2[a] | 3[a] |
| 1.0% SFR Flex | 0 | 0 |

[a]Same sample showed thinning and migration.

CONCLUSIONS

During initial studies, the 0.5% SFR Flex sample had the best handling characteristics. During implantation, the 0.5% SFR Flex samples were easy to manipulate and they conformed very well to the site of implantation. They were also easy to tear to size. However, these samples were inadequate with respect to performance at the three week end-point of the sheep study. Two out of the three 0.5% SFR Flex implants migrated or separated. The one sample that did not migrate exhibited thinning in the inner transverse process (TP) region.

The 0.5% FR Flex (PLLA) samples performed well upon implantation. It was observed that these prototypes were thicker and felt denser than the others. They were initially quite stiff but tore to size with ease. After the three week period there was only thinning in the inter TP space on one sample and a small migration observed in another.

The 1.0% SFR Flex samples were the strongest overall and this was noted during implantation while the surgeons were tearing the strips to size (most difficult but more than manageable). The strips were also not as initially conformable as the others; this was observed as a bounce back away from the bone and tissues after pressing the sample down at the site of implantation. At the three week time point, the 1.0% SFR Flex samples showed the best performance with little to no thinning and absolutely no migration. They also had good vascularization and a good ground substance layer (i.e., the collagenous matrix that is secreted by the osteoblasts and the mineralized material).

The fiberless Flex performed very well during implantation. The strips were quite flexible and conformed nicely to the native bone and tissues. After three weeks in vivo, the strips did thin considerably and had also elongated by approximately 10 mm from their original lengths. Vascularization and ground substance formation were also observed.

From these results we conclude that the 1.0% SFR Flex formulation is superior based on its performance in vivo. Based purely on handling, this formulation is not the most ideal in its dry state. It has the lowest tensile elongation and initial conformability. However, after hydration, the handling characteristics of the strips become quite ideal and outperform others; strips conform to the site and do not fall apart during manipulation. Typical human surgical sites are much wetter than the site used for this study and this can minimize any handling problems for this formulation.

EXAMPLE 11

SEM Imaging

Scanning electron microscopy (SEM) measurements were made of silk fiber reinforced Flex formulations with a micron bar incorporated in each image (see FIGS. 6A and 6B). Pore sizes were evaluated using separate views of different SEM images and a calibrated caliper. The measured pore sizes were then normalized against the size bar associated with each photographic image. Mean pore diameter was measured in three separate fields of view for two samples of silk fiber reinforced Flex. In the first sample the mean pore diameter was 96±69 microns. In the second sample the mean pore diameter was 59±31 microns.

The porosity of the formulations can be important for promoting cell and vascular infiltration following implantation into a subject. The observed sizes of the pores present in these materials are sufficient to promote infiltration and bone formation.

EXAMPLE 12

Compression Testing

The purpose of this study was to do a preliminary evaluation of the compressive strength of current 1.0% silk fiber reinforced Flex formulations. This testing was performed using a method similar to the method of Example 2 to gain an understanding of the compressive strength of fiber reinforced Flex in its dry and wet states. The crosshead rate was 0.1 in/min.

Four cylinders of fiber reinforced Flex with 12 mm diameter and 12 mm height were made by packing the fiber reinforced putty into a mold and lyophilizing the putty. Samples were tested dry and wet. The results are depicted in FIG. 7.

From the plot of stress versus strain (see FIG. 7), it is evident that the gel matrix has its own initial reaction to the applied stress (see the region between 0 and approximately 0.08 strain). The particles and fibers then begin to have applied load as evidence by the sharp slope increase and then yield occurs around 1.5 MPa for the dry formulation. The 0.2% strain offset was used to calculate yield strength. The observed modulus (calculated from the slope) was observed to be 14.66 MPa.

From the plot of stress versus strain (see FIG. 7), it is evident that the two wet samples showed a very interesting profile with four distinct regions. The first, between 0 and 0.12 strain is most likely the gel reaction. Second, between 0.12 and 0.27 strain the outer, wet material failed. Third, between 0.27 and 0.45 strain, the inner, dry material began to take on load and failed. Finally, the last sharp increase in slope was the ABM granules in direct contact. The samples had wet yield strength of approximately 0.55 MPa and a modulus of 3.47 MPa.

EXAMPLE 13

Samples Prepared by Rolling Versus Extrusion

The purpose of this study was to compare the stress values of the tensile test to the load values of the ball punch deformation strengths observed for 1.0% silk fiber reinforced Flex (wet and dry) and 1.0% silk fiber reinforced putty in which the samples were prepared (i) by rolling the putty into sheets, or (ii) extruding the putty.

Rolled strips were prepared by making 1.0% silk fiber reinforced putty and rolling the putty to form the desired shape. The strips were then lyophilized to form 1.0% silk fiber reinforced Flex strips (approximate thickness 4 mm).

Extruded strips were prepared by making 1.0% silk fiber reinforced putty and extruding the putty from an orifice 12 mm in diameter into 200 mm long "ropes." The ropes were pressed into a mold and lyophilized to form 1.0% silk fiber reinforced Flex strips (approximate thickness 4 mm). Alternatively, the putties of the invention can be extruded from an orifice of 25 mm×4 mm to form sheets ready for lyophilization.

Tensile strength and modulus were evaluated for rolled and extruded strips of 1.0% silk fiber reinforced putty. The results are provided in Table 8.

TABLE 8

| Sample | Thickness (mm) | Modulus (kPa) | Strength (kPa) | Thickness | Modulus (kPa) | Strength (kPa) |
|---|---|---|---|---|---|---|
| | Rolled 1% SFR Putty (n = 18) | | | Extruded 1% SFR Putty (n = 7) | | |
| Ave | 4.08 | 2011.44 | 401.44 | 3.95 | 4404.29 | 645.29 |
| 95% Conf | 0.03 | 310.89 | 56.19 | 0.01 | 241.39 | 46.61 |
| St. Dev | 0.05 | 672.98 | 121.63 | 0.02 | 325.85 | 62.92 |
| Max | 4.20 | 3468.00 | 635.00 | 3.97 | 4750.00 | 711.00 |
| Min | 3.98 | 773.00 | 191.00 | 3.92 | 3727.00 | 520.00 |

LAF, EAF, and stress were evaluated for rolled and extruded strips of 1.0% silk fiber reinforced dry Flex. The results are provided in Table 9.

TABLE 9

| Sample | Thicknes (mm) | LAF (N) | EAF (mm) | Stress (kPa) | Thickness | LAF (N) | EAF (mm) | Stress (kPa) |
|---|---|---|---|---|---|---|---|---|
| | Rolled 1% SFR Flex DRY (n = 12) | | | | Extruded 1% SFR Flex DRY (n = 11) | | | |
| Ave | 3.95 | 53.29 | 7.51 | 164.99 | 3.95 | 53.92 | 6.43 | 184.73 |
| 95% Conf | 0.01 | 3.57 | 0.22 | 14.43 | 0.01 | 3.19 | 0.33 | 10.35 |
| St. Dev | 0.02 | 6.30 | 0.39 | 25.51 | 0.02 | 5.39 | 0.56 | 17.52 |
| Max | 3.97 | 61.29 | 8.20 | 200.98 | 3.97 | 62.52 | 7.80 | 211.51 |
| Min | 3.92 | 42.20 | 7.00 | 117.05 | 3.92 | 46.41 | 5.75 | 155.72 |

LAF, EAF, and stress were evaluated for rolled and extruded strips of 1.0% silk fiber reinforced wet Flex. The results are provided in Table 10.

TABLE 10

| Sample | Thickness (mm) | LAF (N) | EAF (mm) | Stress (kPa) | Thickness | LAF (N) | EAF (mm) | Stress (kPa) |
|---|---|---|---|---|---|---|---|---|
| | Rolled 1% SFR Flex WET (n = 6) | | | | Extruded 1% SFR Flex WET (n = 6) | | | |
| Ave | 3.95 | 9.50 | 7.81 | 29.91 | 3.95 | 21.91 | 7.12 | 68.81 |
| 95% Conf | 0.01 | 1.07 | 0.59 | 3.68 | 0.01 | 2.28 | 0.84 | 5.00 |
| St. Dev | 0.02 | 1.34 | 0.74 | 4.60 | 0.02 | 2.85 | 1.05 | 6.25 |
| Max | 3.97 | 11.17 | 9.15 | 35.74 | 3.97 | 26.02 | 8.55 | 75.74 |
| Min | 3.92 | 7.67 | 7.05 | 24.00 | 3.92 | 18.35 | 6.05 | 58.69 |

CONCLUSIONS

The rolled strips of 1% SFR Putty were observed to have a tensile strength of 401.44±56.19 kPa and a modulus of 2011.44±310.89 kPa. In contrast, the tensile strength and modulus of the extruded strips of 1% SFR Putty were observed to be 645.29±46.61 kPa and 4404.29±241.39 kPa, respectively. The results show a statistically significant increase in Yield Stress (YS) and modulus for fiber reinforced putties prepared by extrusion processing. The data suggests that extruded fiber reinforced putty is 50% stronger than rolled fiber reinforced putty.

The dry rolled and extruded strips of 1% SFR Flex were (i) observed to have a LAF of 53.29±3.57 N and 53.92±3.19 N, respectively; (ii) observed to have an EAF of 7.51±0.22 mm and 6.43±0.33 mm, respectively; and observed to have stress values of 164.99±14.43 kPa and 184.73±10.35 kPa, respectively. In the dry 1% SFR Flex the extrusion processing produced little or no change in the strength or handling properties of the sample.

The wet rolled and extruded strips of 1% SFR Flex were (i) observed to have a LAF of 9.50±1.07 N and 21.91±2.28 N, respectively; (ii) observed to have an EAF of 7.81±0.59 mm and 7.12±0.84 mm, respectively; and observed to have stress values of 29.91±3.68 kPa and 68.81±5.00 kPa, respectively. The wet rolled samples were observed to be approximately 18% as strong as the dry rolled samples. In contrast, the extruded samples were observed to be approximately 37% as strong as the dry extruded samples. Thus, extrusion processing results in a fiber reinforced Flex product that remains stronger with wetting. The extruded samples were observed to exhibit a significantly higher LAF and stress in comparison to rolled samples. The stress calculation provides a way to estimate the stresses observed on the sample during the deformation testing and provides a measure of the stresses needed to "puncture" the sample. Thus, extrusion processing results in a fiber reinforced Flex product that is more resistant to puncture during implantation.

From this study it is evident that extruded samples are generally stronger and stiffer, in tension, when pulling parallel to the extrusion direction.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A bone repair putty comprising:
   (i) from 25% to 65% (w/w) hydroxyapatite particles having diameters between 200 microns to 425 microns;
   (ii) from 30% to 75% (w/w) hydrogel carrier for suspending said hydroxyapatite particles; and
   (iii) from 0.2% to 2% (w/w) fibers, said fibers having an average length of from 0.5 to 15 mm and an average diameter of from 5 µm to 30 µm,
   wherein said bone repair putty is non-setting and malleable and wherein the ratio of the number of hydroxyapatite particles to the number of fibers in said putty is from 0.1 to 10.

2. The bone repair putty of claim 1, wherein said hydrogel carrier comprises a dispersing agent selected from glycerin, polyethylene glycol, N-methyl pyrrolidone, and triacetin; a polymer selected from sodium carboxymethylcellulose, polyvinylalcohol, hydroxyethyl cellulose, hydroxypropyl methylcellulose, methylcellulose, ethylcellulose, and hyaluronic acid; and water.

3. The bone repair putty of claim 2, wherein said bone repair putty comprises from 40% to 60% (w/w) hydroxyapatite particles and a hydrogel carrier comprising components present in said bone repair putty in the following amounts:
   (a) from 3% to 10% (w/w) a dispersing agent selected from glycerin, polyethylene glycol, N-methyl pyrrolidone, and triacetin;
   (b) from 0.5% to 2.0% (w/w) a polymer selected from sodium carboxymethylcellulose, polyvinylalcohol, hydroxyethyl cellulose, hydroxypropyl methylcellulose, methylcellulose, ethylcellulose, and hyaluronic acid; and
   (c) from 25% to 55% (w/w) water.

4. The bone repair putty of claim 3, wherein said hydroxyapatite particles have diameters between 250 microns to 425 microns.

5. The bone repair putty of claim 4, wherein said hydroxyapatite particles are anorganic bone mineral coated with P-15 peptide.

6. The bone repair putty of claim 3, wherein said polymer is sodium carboxymethylcellulose and said dispersing agent is glycerin.

7. The bone repair putty of claim 3, wherein said bone repair putty comprises from 45% to 65% (w/w) anorganic bone mineral particles and a hydrogel carrier comprising components present in said bone repair putty in the following amounts:
   (x) from 4.5% to 7.5% (w/w) glycerin;
   (y) from 1.0% to 2.0% (w/w) sodium carboxymethylcellulose; and
   (z) from 35% to 45% (w/w) water.

8. The bone repair putty of claim 7, wherein said fibers are selected from silk fibers, cellulose fibers, nylon fibers, collagen fibers, elastin fibers, gelatin fibers, keratin fibers, hyaluronan fibers, alginate fibers, glyco-lactide fibers, chitosan fibers, polyethylene fibers, polyurethane fibers, polyglycolide fibers, poly-l-lactide fibers, poly-β-hydroxybutyric acid fibers, polydioxanone fibers, polyester fibers, polycarbonate fibers, dacron fibers, bio-active glass fibers, gold fibers, carbon fibers, nitinol fibers, and stainless steel fibers.

9. The bone repair putty of claim 7, comprising from 0.75% to 1.25% (w/w) silk fibers, said fibers having an average length of from 7 to 12 mm.

10. The bone repair putty of claim 9, wherein said fibers have a diameter of from 5 µm to 20 µm.

11. The bone repair putty of claim 8 or 9, wherein the ratio of the number of anorganic bone mineral particles to the number of fibers in said putty is from 0.25 to 4.

12. The bone repair putty of claim 1, wherein said bone repair putty is extrusion processed.

13. The bone repair putty of claim 1, wherein said bone repair putty exhibits reduced migration in vivo, exhibits no migration in vivo, or exhibits a reduced extrusion time in vitro in comparison to the bone repair putty without said fibers.

14. A composition according to claim 1, wherein said fibers further comprise a cell adhesion peptide.

15. The composition of claim 14, wherein said cell adhesion peptide comprises an amino acid sequence selected from arginine-glycine-aspartate (RGD) and tyrosine-isoleucine-glycine-serine-arginine (YIGSR) (SEQ ID NO: 21), or said cell adhesion peptide is a collagen mimetic peptide.

16. The composition of claim 15, wherein said cell adhesion peptide is a collagen mimetic peptide comprising an amino acid sequence selected from
    Asp-Gly-Glu-Ala (SEQ ID NO: 14),
    Gly-Phe-hydroxyproline-Gly-Glu-Arg (SEQ ID NO: 16),
    Gly-Leu-hydroxyproline-Gly-Glu-Arg (SEQ ID NO: 17),
    Gly-Met-hydroxyproline-Gly-Glu-Arg (SEQ ID NO: 18),
    Gly-Leu-Ser-Gly-Glu-Arg (SEQ ID NO: 19),
    Gly-Ala-Ser-Gly-Glu-Arg (SEQ ID NO: 19),
    Gly-Ala-hydroxyproline -Gly-Glu-Arg (SEQ ID NO: 20), and
    Gly-Thr-Pro-Gly-Pro-Gln-Gly-Ile-Ala-Gly-Gln-Arg-Gly-Val-Val (P15) (SEQ ID NO: 1),
    or a bioactive fragment thereof.

17. The composition of claim 14, wherein said fibers are silk fibers comprising P-15 peptide.

18. The composition of claim 17, wherein said hydroxyapatite particles are anorganic bone mineral coated with P-15 peptide.

19. A pliable implantable composition for correcting bone defects formed by lyophilizing the bone repair putty of claim 1.

20. The pliable implantable composition of claim 19, wherein said pliable implantable composition has a ratio of $LAF_{dry}$ to $LAF_{wet}$ of from 1.5 to 15.

21. The pliable implantable composition of claim 19, wherein the ratio of $LAF_{FR}$ to $LAF_{fiberless}$ of from 3 to 100.

22. The pliable implantable composition of claim 19, wherein the ratio of $YS_{FR}$ to $YS_{fiberless}$ of from 3 to 15.

23. The pliable implantable composition of claim 19, wherein the ratio of $M_{FR}$ to $M_{fiberless}$ of from 5 to 40.

24. A pliable implantable composition for correcting bone defects comprising:
    (i) from 5% to 20% (w/w) a dispersing agent selected from glycerin, polyethylene glycol, N-methyl pyrrolidone, and triacetin;
    (ii) from 1.0% to 6.0% (w/w) a polymer selected from sodium carboxymethylcellulose, polyvinylalcohol, hydroxyethyl cellulose, hydroxypropyl methylcellulose, methylcellulose, ethylcellulose, and hyaluronic acid;
    (iii) from 65% to 90% (w/w) hydroxyapatite particles having diameters between 200 microns to 425 microns;
    (iv) from 0.2% to 3.5% (w/w) fibers, said fibers having an average length of from 0.5 to 15 mm and an average diameter of from 5 µm to 30 µm; and
    (v) 1.5% to 20% (w/w) water,
    wherein said pliable implantable composition has a porosity of from 5 to 35% and wherein the ratio of the number of calcium phosphate particles to the number of fibers in said pliable implantable composition is from 0.1 to 10.

25. The pliable implantable composition of claim 24, wherein said hydroxyapatite particles have diameters between 250 microns to 425 microns.

26. The pliable implantable composition of claim 24, wherein said hydroxyapatite particles are anorganic bone mineral coated with P-15 peptide.

27. The pliable implantable composition of claim 24, wherein said polymer is sodium carboxymethylcellulose and said dispersing agent is glycerin.

28. The pliable implantable composition of claim 24, wherein said composition comprises:
    (i) from 8% to 15% (w/w) glycerin;
    (ii) from 1.5% to 3.0% (w/w) sodium carboxymethylcellulose;
    (iii) from 75% to 90% (w/w) anorganic bone mineral particles; and
    (iv) from 0.2% to 3.5% (w/w) fibers, said fibers having an average length of from 0.5 to 15 mm; and
    (v) from 1.5% to 6% (w/w) water.

29. The pliable implantable composition of claim 28, wherein said fibers are selected from silk fibers, cellulose fibers, nylon fibers, collagen fibers, elastin fibers, gelatin fibers, keratin fibers, hyaluronan fibers, alginate fibers, glycolactide fibers, chitosan fibers, polyethylene fibers, polyurethane fibers, polyglycolide fibers, poly-l-lactide fibers, poly-β-hydroxybutyric acid fibers, polydioxanone fibers, polyester fibers, polycarbonate fibers, dacron fibers, bio-active glass fibers, gold fibers, carbon fibers, nitinol fibers, and stainless steel fibers.

30. The pliable implantable composition of claim 29, comprising from 1.2% to 1.8% (w/w) silk fibers, said silk fibers having an average length of from 7 to 12 mm.

31. The pliable implantable composition of claim 29 or 30, wherein said fibers have a diameter of from 5 µm to 20 µm.

32. The pliable implantable composition of claim 31, wherein the ratio of the number of anorganic bone mineral particles to the number of fibers in said pliable implantable composition is from 0.25 to 4.

33. The pliable implantable composition of claim 32, wherein said composition is formed by lyophilizing the bone repair putty of claim 12.

34. The pliable implantable composition of claim 33, wherein said pliable implantable composition has a ratio of $LAF_{dry}$ to $LAF_{wet}$ of from 1.5 to 15.

35. The pliable implantable composition of claim 33, wherein the ratio of wet $LAF_{FR}$ to wet $LAF_{fiberless}$ of from 3 to 100.

36. The pliable implantable composition of claim 33, wherein the ratio of $YS_{FR}$ to $YS_{fiberless}$ of from 3 to 15.

37. The pliable implantable composition of claim 33, wherein the ratio of $M_{FR}$ to $M_{fiberless}$ of from 5 to 40.

38. The composition of claim 33, wherein said pliable implantable composition exhibits reduced migration in vivo, exhibits no migration in vivo, or exhibits a reduced extrusion time in vitro in comparison to the pliable implantable composition without said fibers.

* * * * *